US011382706B2

(12) United States Patent
Marshall

(10) Patent No.: US 11,382,706 B2
(45) Date of Patent: Jul. 12, 2022

(54) SECURING AN INTERFACE ELEMENT RAIL OF A ROBOTIC SURGICAL INSTRUMENT INTERFACE

(71) Applicant: CMR Surgical Limited, Cambridge (GB)

(72) Inventor: Keith Marshall, Cambridge (GB)

(73) Assignee: CMR Surgical Limited, Cambridge (GB)

( * ) Notice: Subject to any disclaimer, the term of this patent is extended or adjusted under 35 U.S.C. 154(b) by 215 days.

(21) Appl. No.: 16/620,331

(22) PCT Filed: Jun. 6, 2018

(86) PCT No.: PCT/GB2018/051545
§ 371 (c)(1),
(2) Date: Dec. 6, 2019

(87) PCT Pub. No.: WO2018/224828
PCT Pub. Date: Dec. 13, 2018

(65) Prior Publication Data
US 2020/0197110 A1  Jun. 25, 2020

(30) Foreign Application Priority Data

Jun. 6, 2017 (GB) .................................... 1709017

(51) Int. Cl.
*A61B 34/30* (2016.01)
*A61B 34/00* (2016.01)
(Continued)

(52) U.S. Cl.
CPC .............. *A61B 34/30* (2016.02); *A61B 17/29* (2013.01); *A61B 34/71* (2016.02); *B25J 9/0009* (2013.01);
(Continued)

(58) Field of Classification Search
CPC ......... A61B 34/30; A61B 34/37; A61B 34/70; A61B 34/71; A61M 25/0133; A61M 25/0136; F16B 5/02; F16B 9/054
See application file for complete search history.

(56) References Cited

U.S. PATENT DOCUMENTS

2006/0264819 A1\* 11/2006 Fischer ............. A61M 25/0147
604/95.04
2009/0247942 A1  10/2009 Kirschenman
(Continued)

FOREIGN PATENT DOCUMENTS

CN  102405021 B  7/2014
EP  0880337 B1  11/2004
(Continued)

OTHER PUBLICATIONS

Search Report issued in corresponding GB Patent Application No. 1709017.6, dated Nov. 29, 2017.
(Continued)

*Primary Examiner* — Wade Miles
(74) *Attorney, Agent, or Firm* — Renner, Otto, Boisselle & Sklar, LLP

(57) ABSTRACT

A robotic surgical instrument, comprising: a shaft; an articulation at a distal end of the shaft for articulating an end effector, the articulation being driveable by a pair of driving elements; and an instrument interface at a proximal end of the shaft, the instrument interface comprising: a chassis; an instrument interface element slideable along a guide bar for driving the pair of driving elements, wherein the pair of driving elements are fast with respect to the interface element so that a displacement of the instrument interface element with respect to the guide bar is transferred to the pair of driving elements; the chassis comprising a support element configured to interface the guide bar along at least
(Continued)

a portion of its length; and a securing element for retaining the guide bar against the support element to thereby secure the guide bar to the chassis.

20 Claims, 18 Drawing Sheets

(51) Int. Cl.
    *A61B 17/29* (2006.01)
    *B25J 9/10* (2006.01)
    *B25J 15/00* (2006.01)
    *B25J 17/02* (2006.01)
    *B25J 9/00* (2006.01)
    *A61B 17/00* (2006.01)

(52) U.S. Cl.
    CPC ............ *B25J 9/104* (2013.01); *B25J 9/1045* (2013.01); *B25J 15/0028* (2013.01); *B25J 17/02* (2013.01); *B25J 17/0283* (2013.01); *A61B 2017/00477* (2013.01); *A61B 2017/2927* (2013.01); *A61B 2017/2929* (2013.01); *A61B 2017/2932* (2013.01); *A61B 2017/2938* (2013.01); *A61B 2034/302* (2016.02); *A61B 2034/305* (2016.02); *A61B 2034/306* (2016.02); *A61B 2034/715* (2016.02)

(56) References Cited

U.S. PATENT DOCUMENTS

| | | | |
|---|---|---|---|
| 2009/0281524 A1* | 11/2009 | Scheibe | ............ A61M 25/0136 604/528 |
| 2011/0167945 A1 | 7/2011 | Yang et al. | |
| 2013/0158565 A1 | 6/2013 | Anvari et al. | |
| 2014/0276942 A1 | 9/2014 | Kirschenman et al. | |
| 2016/0206853 A1* | 7/2016 | Bolduc | ............ A61M 25/0147 |
| 2016/0310700 A1* | 10/2016 | Drake | ............ A61M 25/0097 |
| 2017/0022656 A1 | 1/2017 | Crawford et al. | |
| 2017/0027656 A1 | 2/2017 | Robert et al. | |

FOREIGN PATENT DOCUMENTS

| | | |
|---|---|---|
| GB | 2546392 | 7/2017 |
| JP | S5882688 A | 5/1983 |
| JP | S61100335 A | 5/1986 |
| JP | 2015037549 A | 2/2015 |
| JP | 2015107340 A | 6/2015 |
| WO | 2010123231 A2 | 10/2010 |
| WO | 2016090459 A1 | 6/2016 |
| WO | 2017/098266 | 6/2017 |

OTHER PUBLICATIONS

International Search Report issued in corresponding International Patent Application No. PCT/GB2018/051545 dated Mar. 8, 2018.
Examination Report dated Nov. 16, 2021, for corresponding Australian Patent Application No. 2018280956.
Examination Report dated Oct. 29, 2021 in corresponding Indian Application No. 201927054504.
Decision to Grant a Patent dated Apr. 22, 2022, for corresponding Japanese Patent Application No. 2019-567248.

* cited by examiner

SECURING AN INTERFACE ELEMENT RAIL OF A ROBOTIC SURGICAL INSTRUMENT INTERFACE

FIELD

This invention relates to securing a rail supporting a moveable interface element of a robotic surgical instrument interface.

BACKGROUND

It is known to use robots for assisting and performing surgery. FIG. 1 illustrates a typical surgical robot 100 which consists of a base 108, an arm 102, and an instrument 105. The base supports the robot, and is itself attached rigidly to, for example, the operating theatre floor, the operating theatre ceiling or a trolley. The arm extends between the base and the instrument. The arm is articulated by means of multiple flexible joints 103 along its length, which are used to locate the surgical instrument in a desired location relative to the patient. The surgical instrument is attached to the distal end 104 of the robot arm. The surgical instrument penetrates the body of the patient 101 at a port 107 to access the surgical site. At its distal end, the instrument comprises an end effector 106 for engaging in a medical procedure.

FIG. 2 illustrates a typical surgical instrument 200 for performing robotic laparoscopic surgery. The surgical instrument comprises a base 201 by means of which the surgical instrument connects to the robot arm. A shaft 202 extends between base 201 and articulation 203. Articulation 203 terminates in an end effector 204. In FIG. 2, a pair of serrated jaws are illustrated as the end effector 204. The articulation 203 permits the end effector 204 to move relative to the shaft 202. It is desirable for at least two degrees of freedom to be provided to the motion of the end effector 204 by means of the articulation.

FIG. 3 illustrates an example of a known surgical instrument 300 in which end effector 204 is permitted to move relative to shaft 202 by means of pitch joint 301 and two yaw joints 302. Joint 301 enables the end effector 204 to rotate about pitch axis 303. Joints 302 enable each jaw of the end effector 204 to rotate about yaw axis 304. The joints are driven by cables 306, 307 and 308. Pulley 305 is used to direct cables 307 and 308 from their passage over the pitch joint to the yaw joints. Pulley 305 is offset from the central axis of the articulation 203.

In a typical laparoscopy operation, a surgeon utilises many instruments, and hence exchanges one instrument for another many times. It is therefore desirable to minimise the time taken and maximise the ease with which one instrument is detached from a robot arm and a different instrument is attached. Additionally, it is desirable to minimise the time taken in setting up the instrument ready for use once it has been attached to the robot arm.

As such, the surgical instrument 300 may be attached at its proximal end to the distal end of the robotic arm by an instrument interface. The instrument interface may connect, or engage with, an interface of the robotic arm. Mechanical drive to drive the joints of the instrument (e.g. joints 301 and 302) may be transferred to the instrument from the robotic arm via the robotic arm interface and the instrument interface.

SUMMARY

According to one aspect of the present disclosure there is provided A robotic surgical instrument, comprising: a shaft; an articulation at a distal end of the shaft for articulating an end effector, the articulation being driveable by a pair of driving elements; and an instrument interface at a proximal end of the shaft, the instrument interface comprising: a chassis; an instrument interface element slideable along a guide bar for driving the pair of driving elements, wherein the pair of driving elements are fast with respect to the interface element so that a displacement of the instrument interface element with respect to the guide bar is transferred to the pair of driving elements; the chassis comprising a support element configured to interface the guide bar along at least a portion of its length; and a securing element for retaining the guide bar against the support element to thereby secure the guide bar to the chassis.

The support element may comprise a curved surface that interfaces the guide bar along at least a portion of its length.

The support element may be arranged so that each surface normal to the curved surface is transverse to a longitudinal axis of the guide bar.

The support element may be a corner feature defining a corner, and the securing element retains the guide bar in the corner to secure the guide bar to the chassis.

The corner feature may comprise two surfaces that define the corner.

The two surfaces may be planar.

The two surfaces may be transverse to each other.

The angle between the two surfaces may be less than 180 degrees.

The angle between the two surfaces may be greater than or equal to 90 degrees and less than 180 degrees.

The angle between the two surfaces may be less than or equal to 90 degrees.

The two surfaces may meet to define a join that is parallel to a longitudinal axis of the instrument shaft.

The securing element may comprise a shaft portion and a conical-shaped head, the shaft portion being inserted into the chassis to secure the guide bar to the chassis.

The shaft portion may be inserted into the chassis parallel to one of the surfaces of the corner feature.

The shaft portion may be inserted into the chassis so that the conical-shaped head secures the guide bar against the two surfaces of the corner feature.

The shaft portion may be a threaded shaft portion.

The securing element may be a countersunk screw or bolt.

The securing element may comprise a shaft and a head, the shaft being inserted into the corner feature at an angle to both surfaces of the corner feature so that a longitudinal axis of the shaft is non-parallel to both surfaces.

The shaft may be inserted into the corner feature diagonally to the surfaces of the corner feature.

The securing element may be a pan-head bolt.

The securing element may comprise a retaining element having a first surface shaped to engage the guide bar and being secured to the chassis to thereby secure the guide bar to the chassis.

The retaining element may be a block comprising second and third surfaces angled to interface the surfaces of the corner feature.

The securing element may be secured to the chassis by one or more bolts or screws.

The guide bar may comprise a bore, and the securing element may be a screw or bolt inserted into the support element through the bore to secure the guide bar to the chassis.

The instrument interface element may be linearly slideable along the guide bar.

The instrument interface element may be linearly slideable along a longitudinal axis of the guide bar parallel to a longitudinal axis of the shaft.

The instrument interface may further comprise a second securing element to secure the guide bar to the chassis.

The two securing elements may be located at opposing ends of the guide bar.

The chassis may comprise a second support element, and the second securing element may retain the guide bar against the second support element to secure the guide bar to the chassis.

BRIEF DESCRIPTION OF DRAWINGS

The present disclosure will now be described by way of example with reference to the accompanying drawings. In the drawings.

DETAILED DESCRIPTION

The present disclosure is directed to securing a rail supporting a moveable interface element of a robotic surgical instrument interface.

A surgical robotic arm can be attached at its distal end to a surgical instrument. The surgical instrument is typically detachable from the robotic arm, e.g. to facilitate the changeover of instruments during a surgical procedure. The surgical instrument may attach to the distal end of the robotic arm via an instrument interface located at the proximal end of the instrument. The instrument interface can engage an interface located at the distal end of the robotic arm. Surgical instruments may comprise an articulation at their distal end for articulating the instrument's end effectors relative to the instrument shaft. The articulation may comprise one or more joints that are mechanically driven. The drive for the joints may be provided by a drive assembly in the robotic arm, for example to save weight in the instrument. In such an arrangement, it is necessary to transfer the drive from the robotic arm to the joints of the instrument articulation. One approach to do this is to transfer the drive via the robotic arm and instrument interfaces. The instrument interface can comprise moveable interface elements (i.e., moveable relative to the instrument interface). Each interface element can be coupled to a joint of the instrument articulation by a pair of driving elements (e.g., cables). Displacement of the instrument interface elements can then cause movement of the driving elements which drives rotation about a joint. The instrument interface elements may be displaced by mechanically engaging the elements with interface elements of the robotic arm interface which are driven by the drive assembly.

The instrument interface elements can be slideable along a rail, or bar that guides the displacement of the interface elements when they are driven by the drive assembly. That is, the instrument interface elements can be slideably mounted to the rail, or bar. If the rail is not securely fixed in place, the operation of the surgical instrument may be compromised. The present disclosure describes approaches for securing the rail relative to the instrument interface.

Figure 4:
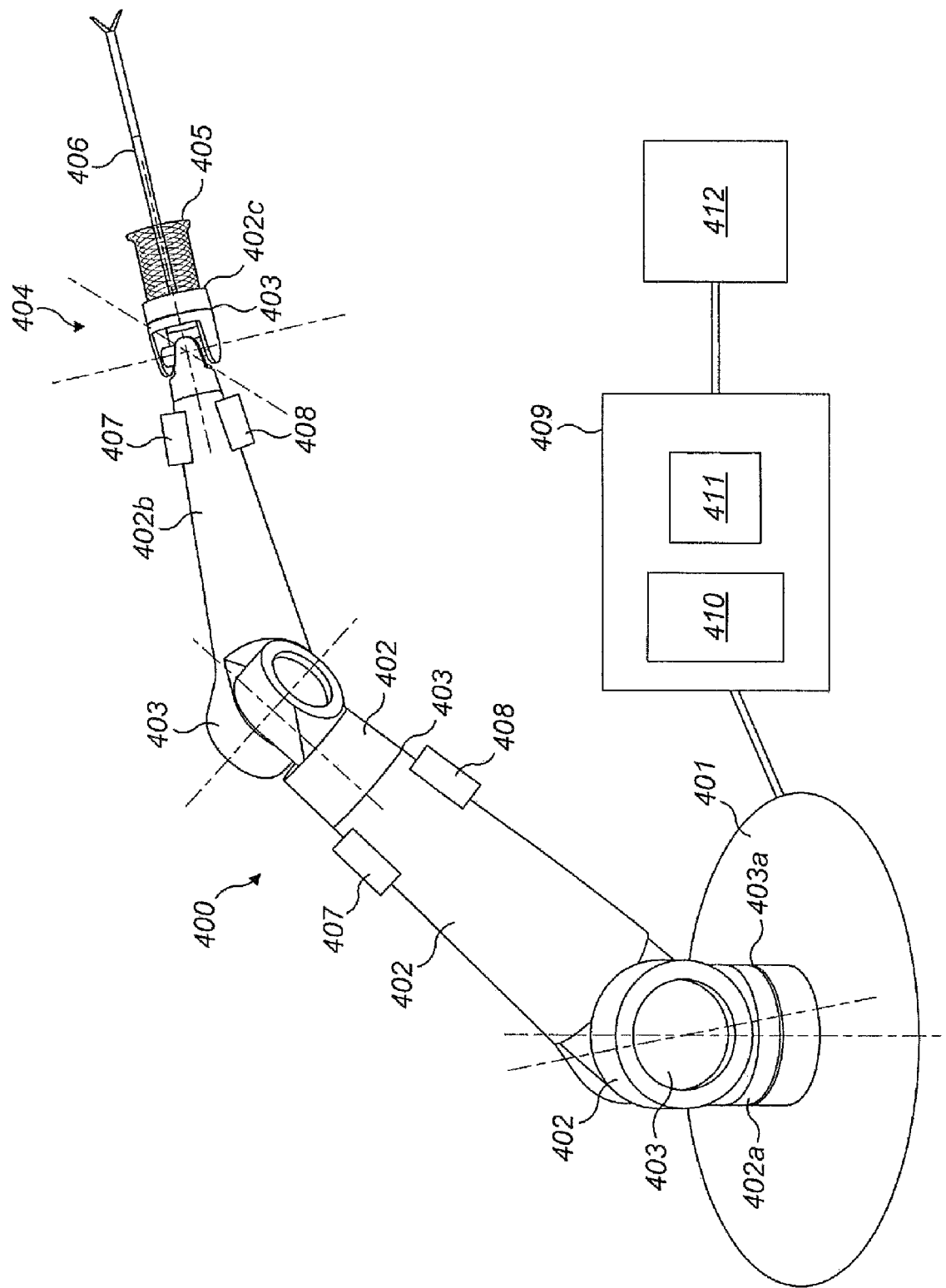
FIG. 4 illustrates a surgical robot.

FIG. 4 illustrates a surgical robot having an arm 400 which extends from a base 401. The arm comprises a number of rigid limbs 402. The limbs are coupled by revolute joints 403. The most proximal limb 402a is coupled to the base by joint 403a. It and the other limbs are coupled in series by further ones of the joints 403. A wrist 404 is made up of four individual revolute joints. The wrist 404 couples one limb (402b) to the most distal limb (402c) of the arm. The most distal limb 402c carries an attachment 405 for a surgical instrument 406. Each joint 403 of the arm has one or more motors 407 which can be operated to cause rotational motion at the respective joint, and one or more position and/or torque sensors 408 which provide information regarding the current configuration and/or load at that joint. The motors may be arranged proximally of the joints whose motion they drive, so as to improve weight distribution. For clarity, only some of the motors and sensors are shown in FIG. 4. The arm may be generally as described in our co-pending patent application PCT/GB2014/053523.

Figure 1:
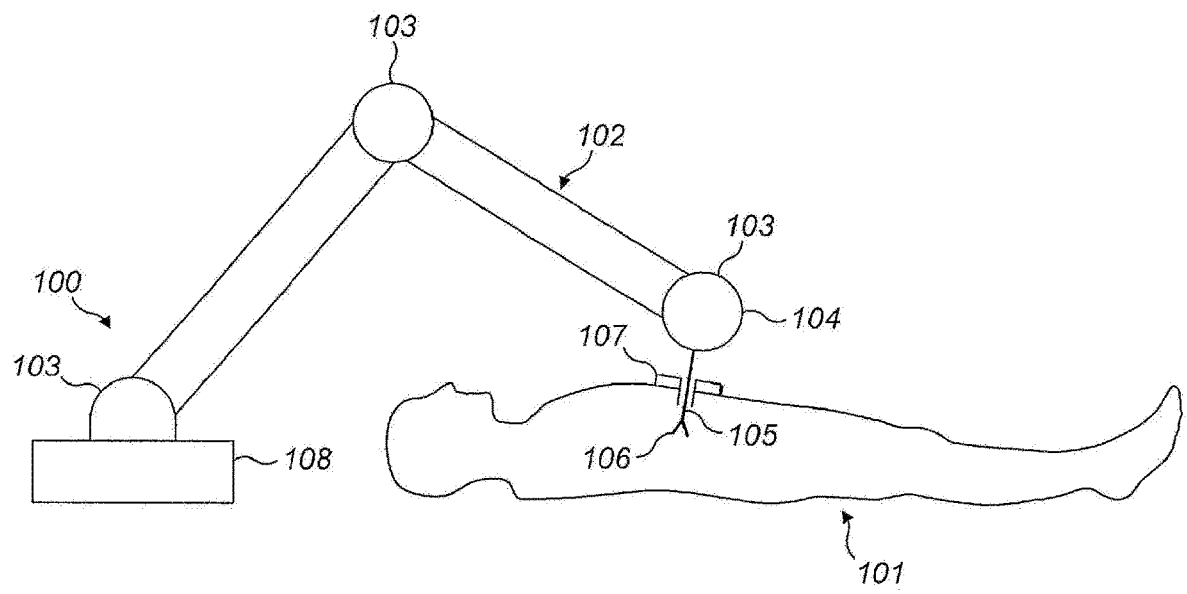
FIG. 1 illustrates a surgical robot performing a surgical procedure.
Figure 2:
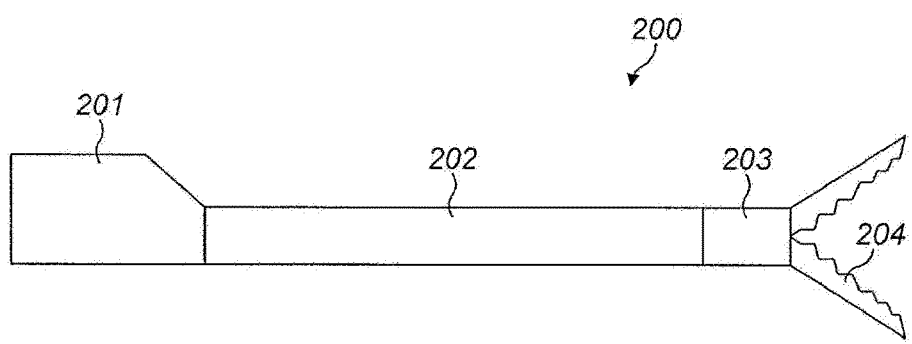
FIG. 2 illustrates a known surgical instrument.
Figure 3:
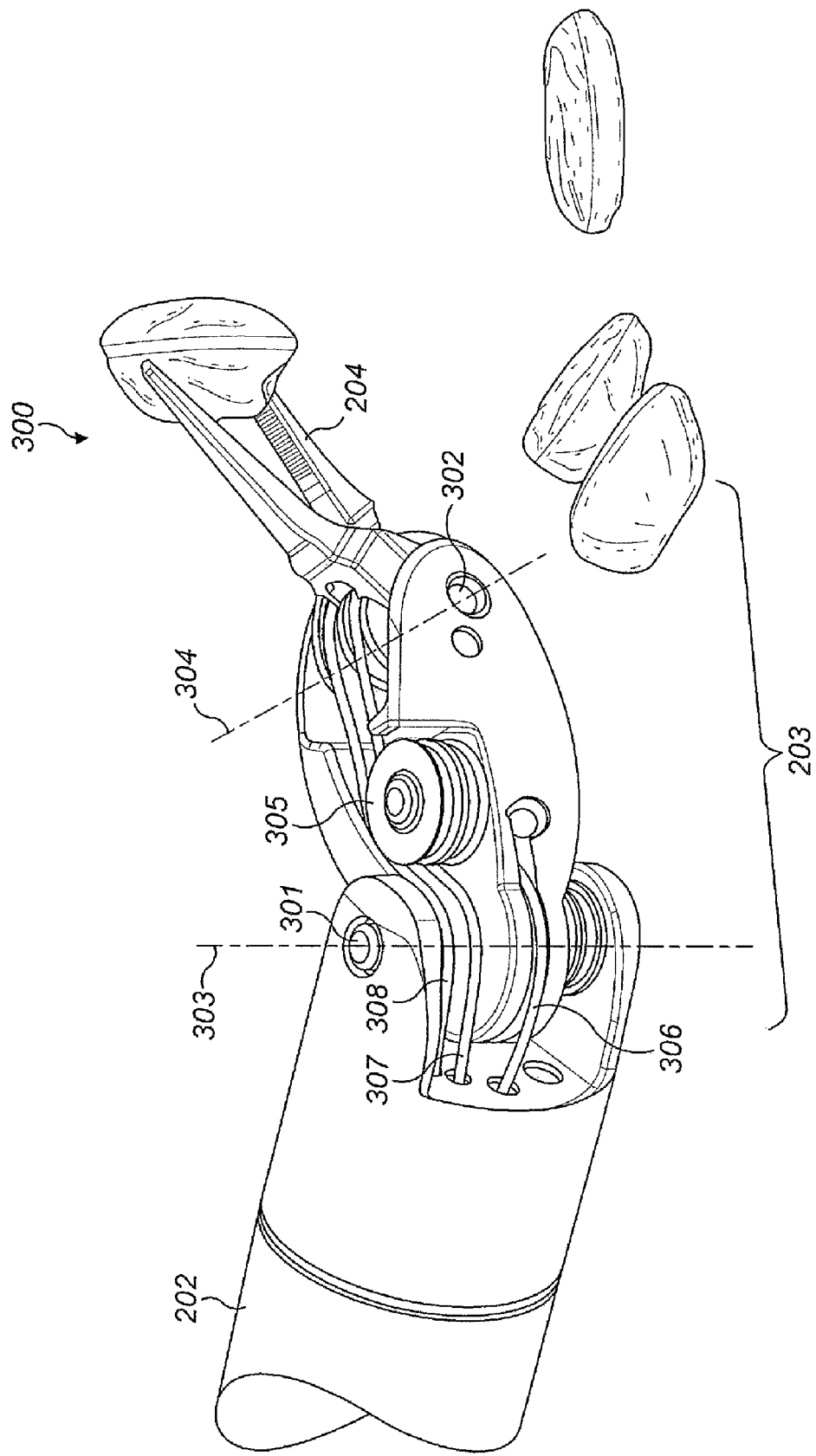
FIG. 3 illustrates a known arrangement of an articulated end effector of a surgical instrument.

The arm terminates in an attachment 405 for interfacing with the instrument 406. The instrument 406 may take the form described with respect to FIG. 2. The attachment 405 comprises a drive assembly for driving articulation of the instrument, and a drive assembly interface for engaging an instrument interface of the instrument 406. Movable interface elements of the drive assembly interface mechanically engage corresponding movable interface elements of the instrument interface in order to transfer drive from the robot arm to the instrument. One instrument may be exchanged for another several times during a typical operation. Thus, the instrument is attachable and detachable from the robot arm during the operation. Features of the drive assembly interface and the instrument interface may aid their alignment when brought into engagement with each other, so as to reduce the accuracy with which they need to be aligned by the user.

The instrument 406 comprises an end effector for performing an operation. The end effector may take any suitable form. For example, the end effector may be smooth jaws, serrated jaws, a gripper, a pair of shears, a needle for suturing, a camera, a laser, a knife, a stapler, a cauteriser, a suctioner. As described with respect to FIG. 2, the instrument comprises an articulation between the instrument shaft and the end effector. The articulation may comprise one or more joints which permit the end effector to move relative to the shaft of the instrument. The one or more joints in the articulation are actuated by driving elements, such as cables. These driving elements are secured at the other end of the instrument shaft to the interface elements of the instrument interface. Thus, the robot arm transfers drive to the end effector as follows: movement of a drive assembly interface element moves an instrument interface element which moves a driving element which moves a joint of the articulation which moves the end effector.

Controllers for the motors, torque sensors and encoders are distributed with the robot arm. The controllers are connected via a communication bus to control unit 409. A control unit 409 comprises a processor 410 and a memory 411. Memory 411 stores in a non-transient way software that is executable by the processor to control the operation of the motors 407 to cause the arm 400 to operate in the manner described herein. In particular, the software can control the processor 410 to cause the motors (for example via distributed controllers) to drive in dependence on inputs from the sensors 408 and from a surgeon command interface 412. The control unit 409 is coupled to the motors 407 for driving them in accordance with outputs generated by execution of the software. The control unit 409 is coupled to the sensors 408 for receiving sensed input from the sensors, and to the command interface 412 for receiving input from it. The respective couplings may, for example, each be electrical or optical cables, or may be provided by a wireless connection. The command interface 412 comprises one or more input devices whereby a user can request motion of the end effector in a desired way. The input devices could, for example, be manually operable mechanical input devices such as control handles or joysticks, or contactless input devices such as optical gesture sensors. The software stored in memory 411 is configured to respond to those inputs and cause the joints of the arm and instrument to move accordingly, in compliance with a pre-determined control strategy. The control strategy may include safety features which moderate the motion of the arm and instrument in response to command inputs. Thus, in summary, a surgeon at the command interface 412 can control the instrument 406 to move in such a way as to perform a desired surgical procedure. The control unit 409 and/or the command interface 412 may be remote from the arm 400.

Figures 5A, 5B:
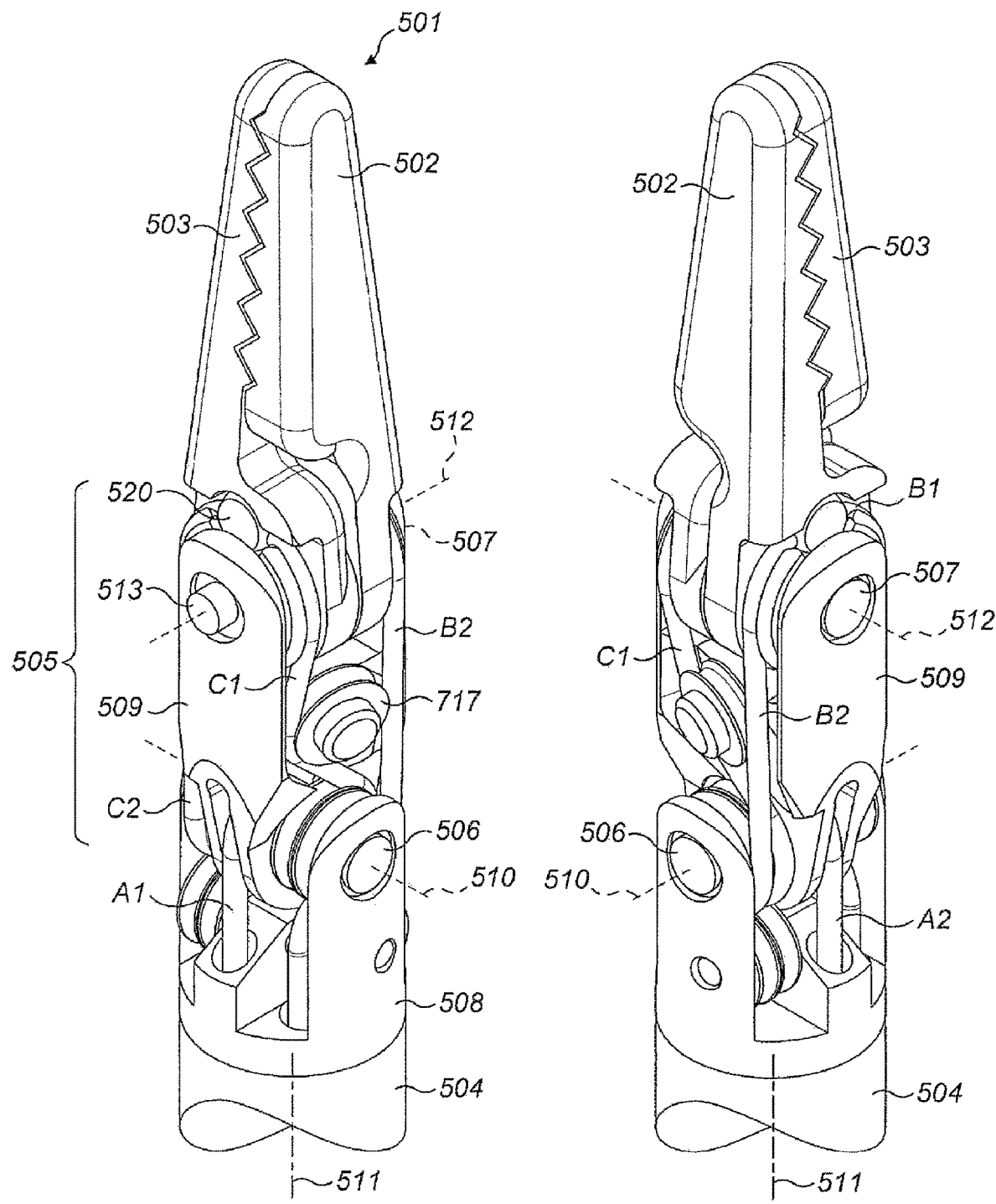
FIGS. 5a and 5b illustrate a distal end of a surgical instrument.

FIGS. 5a and 5b illustrate opposing views of the distal end of an example surgical instrument. In FIGS. 5a and 5b, the end effector 501 comprises a pair of end effector elements 502, 503, which in this example are depicted as a pair of opposing serrated jaws. It will be understood that this is for illustrative purposes only. The end effector may take any suitably form, such as those described above. The end effector 501 is connected to the instrument shaft 504 by articulation 505. Articulation 505 comprises joints which permit the end effector 501 to move relative to the shaft 504. In this example, the articulation 505 comprises three joints. A first joint 506 permits the end effector 501 to rotate about a first axis 510. The first axis 510 is transverse to the longitudinal axis of the shaft 511. The first joint 506 is arranged so that the shaft 504 terminates at its distal end in the joint 506. A second joint 507 permits the first end effector element 502 to rotate about a second axis 512. The second axis 512 is transverse to the first axis 510. A third joint 513 permits the second end effector element 503 to rotate about the second axis 512.

The first end effector element 502 and the second end effector element 503 may be independently rotatable about the second axis 512 by the second and third joints. The end effector elements may be rotated in the same direction or different directions by the second and third joints. The first end effector element 502 may be rotated about the second axis, whilst the second end effector element 503 is not rotated about the second axis. The second end effector element 503 may be rotated about the second axis, whilst the first end effector element 502 is not rotated about the second axis.

FIGS. 5a and 5b depict a straight configuration of the surgical instrument in which the end effector is aligned with the shaft 504. In this orientation, the longitudinal axis of the shaft 511 is coincident with the longitudinal axis of the articulation and the longitudinal axis of the end effector. Articulation of the first, second and third joints enables the end effector to take a range of attitudes relative to the shaft.

The articulation 505 comprises a supporting body 509. At one end, the supporting body 509 is connected to the shaft 504 by the first joint 506. At its other end, the supporting body 509 is connected to the end effector 501 by second joint 507 and third joint 513. Thus, first joint 506 permits the supporting body 509 to rotate relative to the shaft 504 about the first axis 510; and the second joint 507 and third joint 513 permit the end effector elements 502, 503 to rotate relative to the supporting body 509 about the second axis 512.

In the figures, the second joint 507 and third joint 513 both permit rotation about the same axis 512. However, the second and third joints may alternatively permit rotation of the end effector elements about different axes. The axis of rotation of one of the end effector elements may be offset in the longitudinal direction of the shaft 504 from the axis of rotation of the other end effector element. The axis of rotation of one of the end effector elements may be offset in a direction transverse to the longitudinal direction of the shaft 504 from the axis of rotation of the other end effector element. The axis of rotation of one of the end effector elements may not be parallel to the axis of rotation of the other end effector element. The axes of rotation of the end effector elements 502, 503 may be offset in the longitudinal direction of the shaft and/or offset in a direction perpendicular to the longitudinal direction of the shaft and/or angled with respect to each other. This may be desirable as a result of the end effector elements being asymmetric. For example, in an electrosurgical element, a first end effector element may be powered and a second end effector element not powered and insulated from the first end effector element. To aid this, the axes of rotation of the two end effector elements may be offset in the direction perpendicular to the longitudinal direction of the shaft. In another example, a first end effector element may be a blade and a second end effector element a flat cutting surface. To aid use of the blade, the axes of rotation of the two end effector elements may be angled to one another.

The joints of the articulation 505 are driven by driving elements. The driving elements are elongate elements which extend from the joints in the articulation through the shaft 504 to the instrument interface. Each driving element may be capable of being flexed laterally to its main extent at least in those regions where it engages the internal components of the articulation and instrument interface. In other words, each driving element can be flexed transverse to its longitudinal axis in the specified regions. This flexibility enables the driving elements to wrap around the internal structure of the instrument, such as the joints and pulleys. The driving elements may be wholly flexible transverse to their longitudinal axes. The driving elements may be inflexible along their main extents. The driving elements may resist compression and tension forces applied along their length. In other words, the driving elements may resist compression and tension forces acting in the direction of their longitudinal axes. The driving elements may have a high modulus. The driving elements may remain taut in operation; they may be not permitted to become slack. Thus, the driving elements are able to transfer drive from the instrument interface to the joints. The driving elements may be cables, for example.

Each joint may be driven by a pair of driving elements. Referring to FIGS. 5a and 5b, the first joint 506 is driven by a first pair of driving elements A1,A2. The second joint 507 is driven by a second pair of driving elements B1,B2. The third joint is driven by a third pair of driving elements C1,C2. Each joint of instrument 501 is therefore driven by its own pair of driving elements. In other words, each joint is driven by a dedicated pair of driving elements. The joints may be independently driven. A pair of driving elements may be constructed as a single piece as shown for the third pair of driving elements in FIGS. 5a and 5b. In this case, the single piece is secured to the joint at one point. For example, the third pair of driving elements C1,C2 comprises a ball feature 520 which is secured to the third joint 513. This ensures that when the pair of driving elements is driven, the drive is transferred to motion of the joint about its axis. Alternatively, a pair of driving elements may be constructed as two pieces. In this case, each separate piece is secured to the joint.

Figure 6:
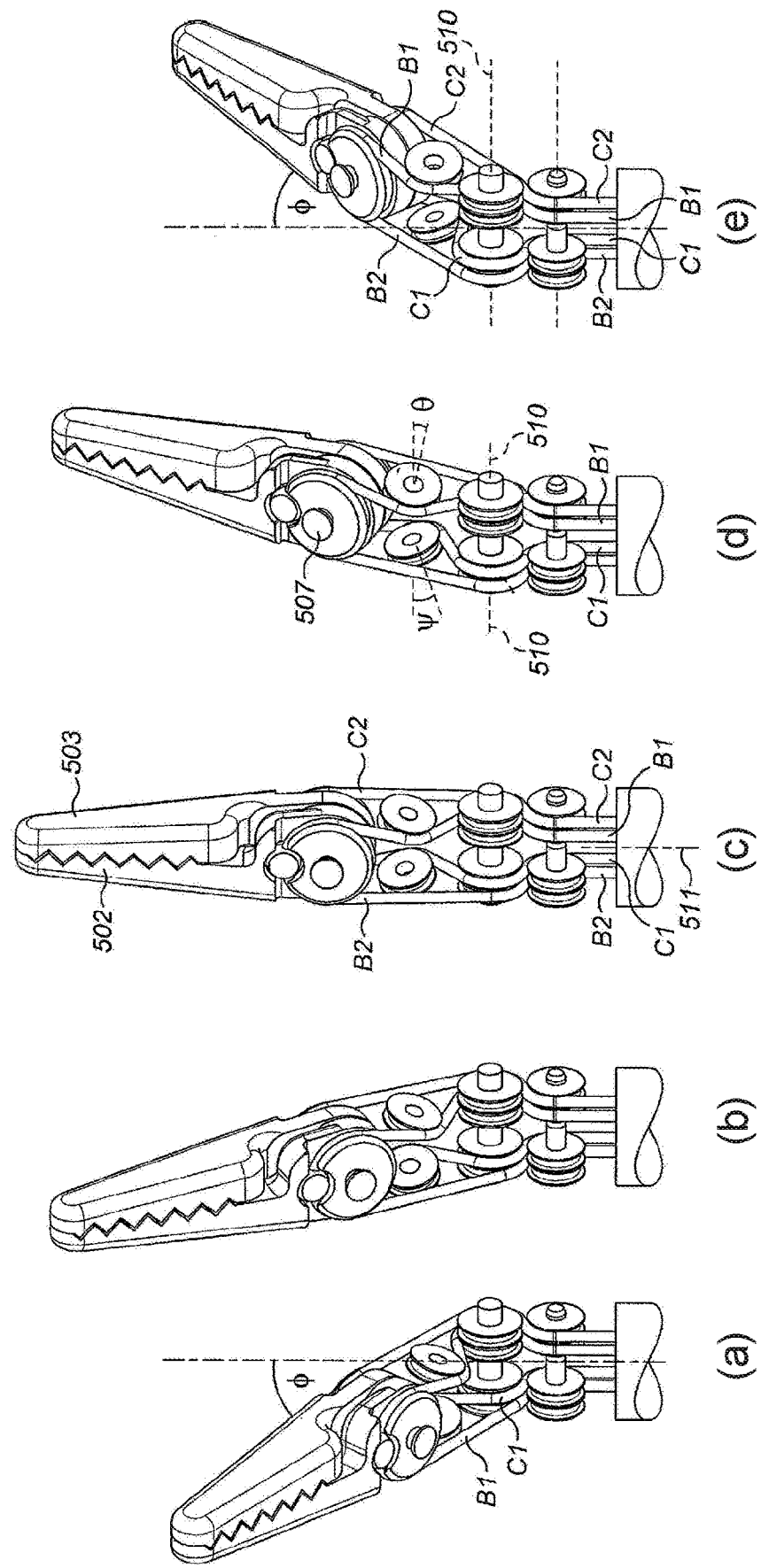
FIG. 6 illustrates a pulley arrangement of the distal end of the surgical instrument of FIGS. 5a and 5b in a variety of non-straight configurations.

FIG. 6 illustrates the distal end of the surgical instrument in five different configurations. Configuration (c) is the straight configuration previously mentioned, in which the end effector is aligned with the instrument shaft. In configurations (a), (b), (d) and (e), rotation about the first joint has occurred relative to configuration (c). In configurations (a), (b), (d) and (e), no rotation about either the second or third joint has occurred relative to configuration (c). Starting from configuration (c), the driving element A2 (not shown) is pulled in order to cause the rotation about the first axis 510 leading to the arrangement of configuration (b). The driving element A2 is further pulled to cause further rotation about the first axis 510 to lead to the arrangement of configuration (a). Starting from configuration (c), the driving element A1 (not shown) is pulled in order to cause rotation about the first axis 510 in an opposing direction to that in configurations (a) and (b), thereby leading to the arrangement of configuration (d). The driving element A1 is further pulled to cause further rotation about the first axis 510 to lead to the arrangement of configuration (e).

Rotation of the end effector 501 about the first axis 510 is bounded by the maximum travel of the first pair of driving elements A1,A2 about the first joint 506. Configuration (a) shows the end effector 501 at maximum rotation about the first axis 510 in one direction, and configuration (e) shows the end effector 501 at maximum rotation about the first axis 510 in the opposing direction. The maximum rotation angle relative to the longitudinal axis of the shaft 511 in both configurations is the angle φ.

The first, second and third pairs of driving elements A1,A2, B1,B2, C1,C2 extend through the instrument shaft from the distal end of the shaft 504 connected to the articulation to the proximal end of the shaft connected to a drive mechanism of the instrument interface.

Figure 7A:
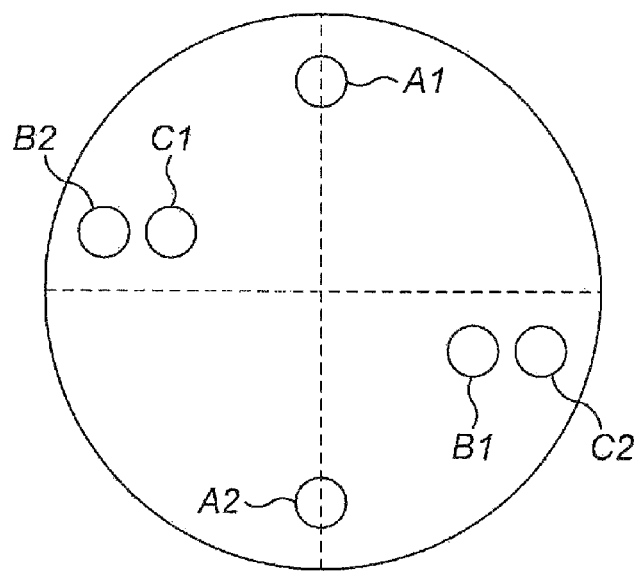
FIG. 7 illustrates arrangements of driving elements in an instrument shaft.
Figure 7B:
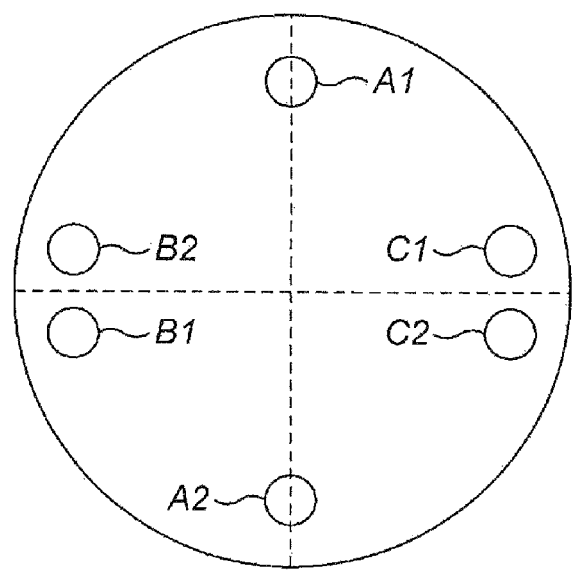
Figure 8A:
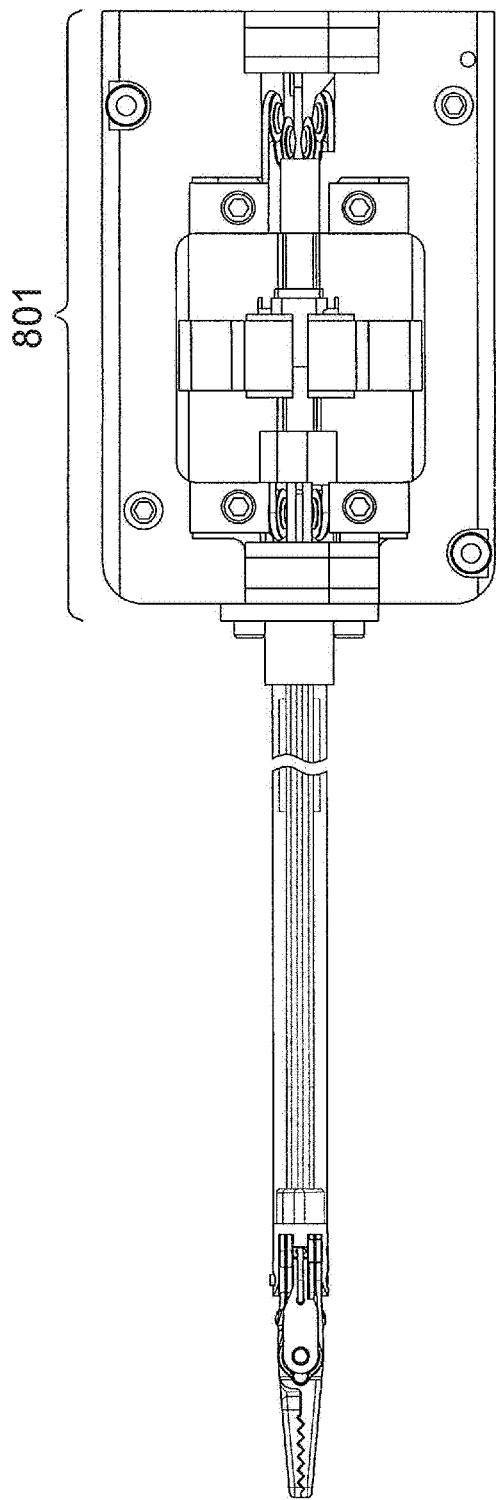
FIGS. 8a and 8b illustrate two views of a surgical instrument including instrument interface.
Figure 8B:
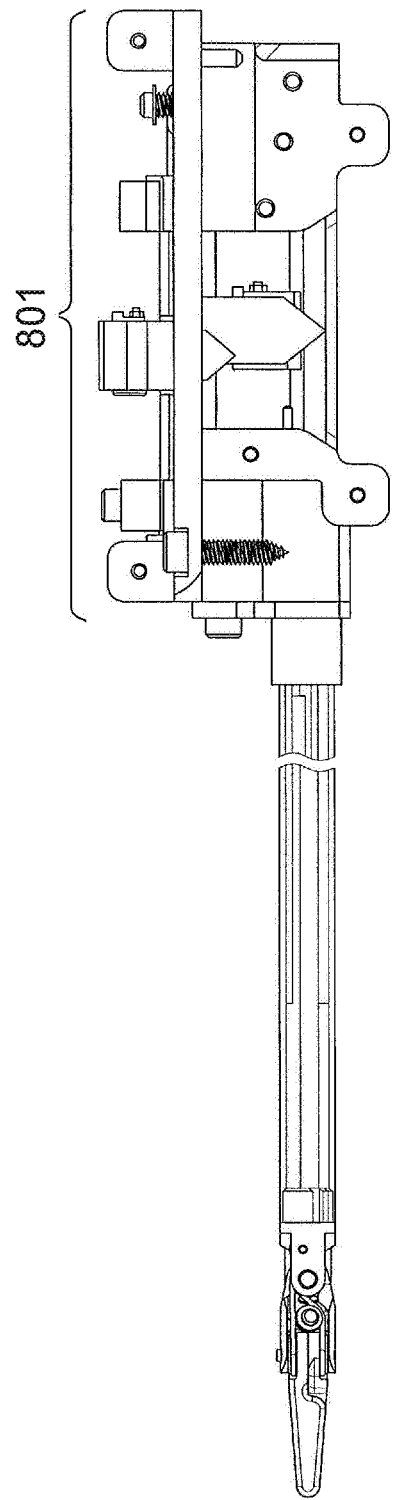

FIGS. 8a and 8b illustrate two views of the first, second and third pairs of driving elements extending from the described articulation to an exemplary instrument interface 801. In an exemplary implementation, the second and third pairs of driving elements overlap in the shaft so as to emerge from the proximal end of the shaft in a different arrangement to that at which they are in at the distal end of the shaft. FIGS. 7a and 7b illustrates cross-sections of the shaft depicting the positions of the driving elements according an exemplary implementation.

FIG. 7a shows a cross-section of the shaft at the distal end of the shaft illustrating the positions of the driving elements. The driving elements A1 and A2 are at opposing sides of the shaft after having left the first joint 506. The driving elements C1 and B2 are adjacent each other on an opposing side of the shaft to the driving elements B1 and C2 which are also adjacent each other. The driving elements C1 and B2 are offset from the driving elements B1 and C2 about an axis 701 which is transverse to the axis 702 connecting driving elements A1 and A2.

FIG. 7b shows a cross-section of the shaft at the proximal end of the shaft illustrating the positions of the driving elements. In other words, configuration (b) shows the positions of the driving elements as they are about to exit the shaft into the instrument interface. The first pair of driving elements A1 and A2 are on opposing sides of the shaft in a similar arrangement to their arrangement in FIG. 7a. The first pair of driving elements may be closer together, by virtue of them having moved slightly towards each other over the course of their extent through the shaft. In FIG. 7b, driving element B1 is located on an opposing side of the shaft to its location in FIG. 7a. In FIG. 7b, driving element C1 is located on an opposing side of the shaft to its location in FIG. 7a. To achieve this, driving element B1 and driving element C1 have not extended down the shaft parallel to the longitudinal axis of the shaft 511. Instead, driving element B1 and driving element C1 have overlapped each other during their extent in the shaft. This overlapping occurs without the driving elements B1 and C1 clashing because of their offset positions in FIG. 7a. Driving element B2 has moved a little in the shaft, but remained on the same side of the shaft as in FIG. 7a, so as to emerge at the proximal end of the shaft adjacent to driving element B1. Driving element C2 has moved a little in the shaft, but remained on the same side of the shaft as in FIG. 7a, so as to emerge at the proximal end of the shaft adjacent to driving element C1.

The driving elements A1, A2, B1, B2, C1 and C2 emerge at the proximal end of the shaft in a configuration which enables them to engage directly with components of the instrument interface.

Referring back to FIGS. 8a and 8b, the instrument interface is relatively flat. The instrument interface extends mostly in a central plane viewed head on in FIG. 8a. The instrument shaft 504 is rigidly attached to the instrument interface 801. The instrument shaft 504 does not rotate or otherwise move relative to the instrument interface 801. The second axis 512 about which the end effector elements 502, 503 rotate is in this example perpendicular to the central plane of the instrument interface. This is the case in the straight configuration of the instrument shown in FIGS. 8a and 8b. Thus, in the straight configuration of the instrument, the jaws of the end effector are moveable in the central plane of the instrument interface.

A driving element may be a uniform component having the same shape and size along its length and constructed of the same material along its length. Alternatively, the driving element may be composed of different portions. In one example, the portion of the driving element which engages components of the instrument interface (such as pulleys and interface elements) is flexible. Similarly, the portion of the driving element which engages components of the distal end of the surgical instrument (such as the pulleys and joints in the articulation) is flexible. Between these two flexible portions are spokes 802 illustrated in FIGS. 8a and 8b. Thus, each pair of driving elements comprises two spokes and two flexible portions. Each pair of driving elements forms a loop. The loop comprises alternating spokes and flexible portions. The two spokes are predominantly or wholly enclosed in the instrument shaft. A distal flexible portion terminates at one end in the distal end of one of the spokes, and at the other end in the distal end of the other spoke. The distal flexible portion engages components of the articulation. A proximal flexible portion terminates at one end in the proximal end of one of the spokes, and at the other end in the proximal end of the other spoke. The proximal flexible portion engages components of the instrument interface. The spokes are stiffer than the flexible portions. Suitably, the spokes are rigid. The spokes may be hollow. Typically, the spokes have a larger diameter than the flexible portions. Thus, the flexible portions may be cables, and the spokes hollow tubes. The flexible portions may terminate where they meet the spokes. Alternatively, the spokes may encapsulate the material of the flexible portions. For example, the spokes may be rigid sheaths which cover flexible cables.

The spokes are stiffer than the flexible portions. Thus, by forming a pair of driving elements from spokes as well as flexible portions, the likelihood of the driving element stretching is reduced. For this reason, the proportion of each driving element which is a spoke is preferably maximised whilst ensuring that the spoke does not come into contact with components of the articulation or the instrument interface, and also that adjacent driving elements do not collide. The spokes are stronger than the flexible portions, and hence more resilient to compression and tension forces applied in any direction than the flexible portions. Thus, by incorporating the spokes, the driving element as a whole is stiffer and less likely to stretch. Thus, the lifetime of the driving element before it needs re-tensioning or replacing is extended.

Mechanical drive from the robotic arm is transferred to the surgical instrument to articulate the joints of the instrument articulation via the instrument interface 801 and drive assembly interface. To drive a joint of the instrument articulation, an interface element of the drive assembly interface is moved, which moves a mechanically engaged interface element of the instrument interface. Movement of the instrument interface element moves a driving element, which drives a joint of the articulation. The mechanism by which the mechanical drive is transferred will be explained in more detail below with reference to FIGS. 9a, 9b and 9c.

Figure 9A:
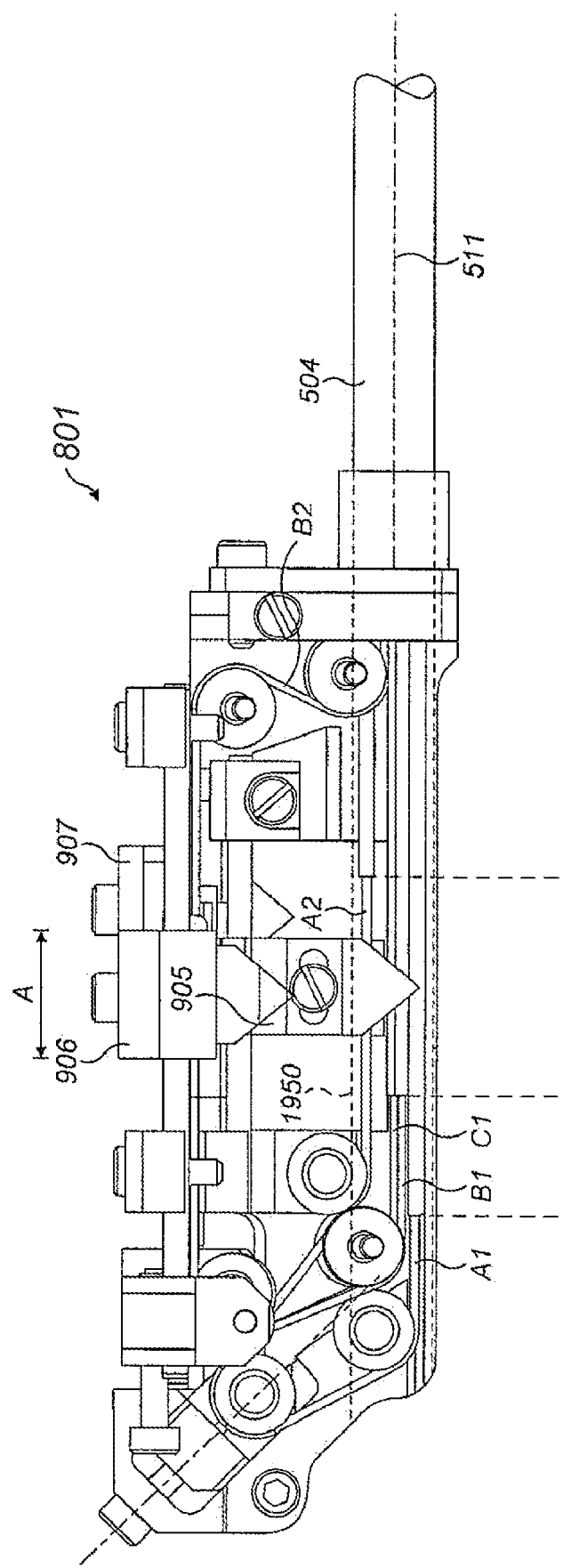
FIGS. 9a, 9b and 9c illustrate three views of an instrument interface.
Figure 9B:
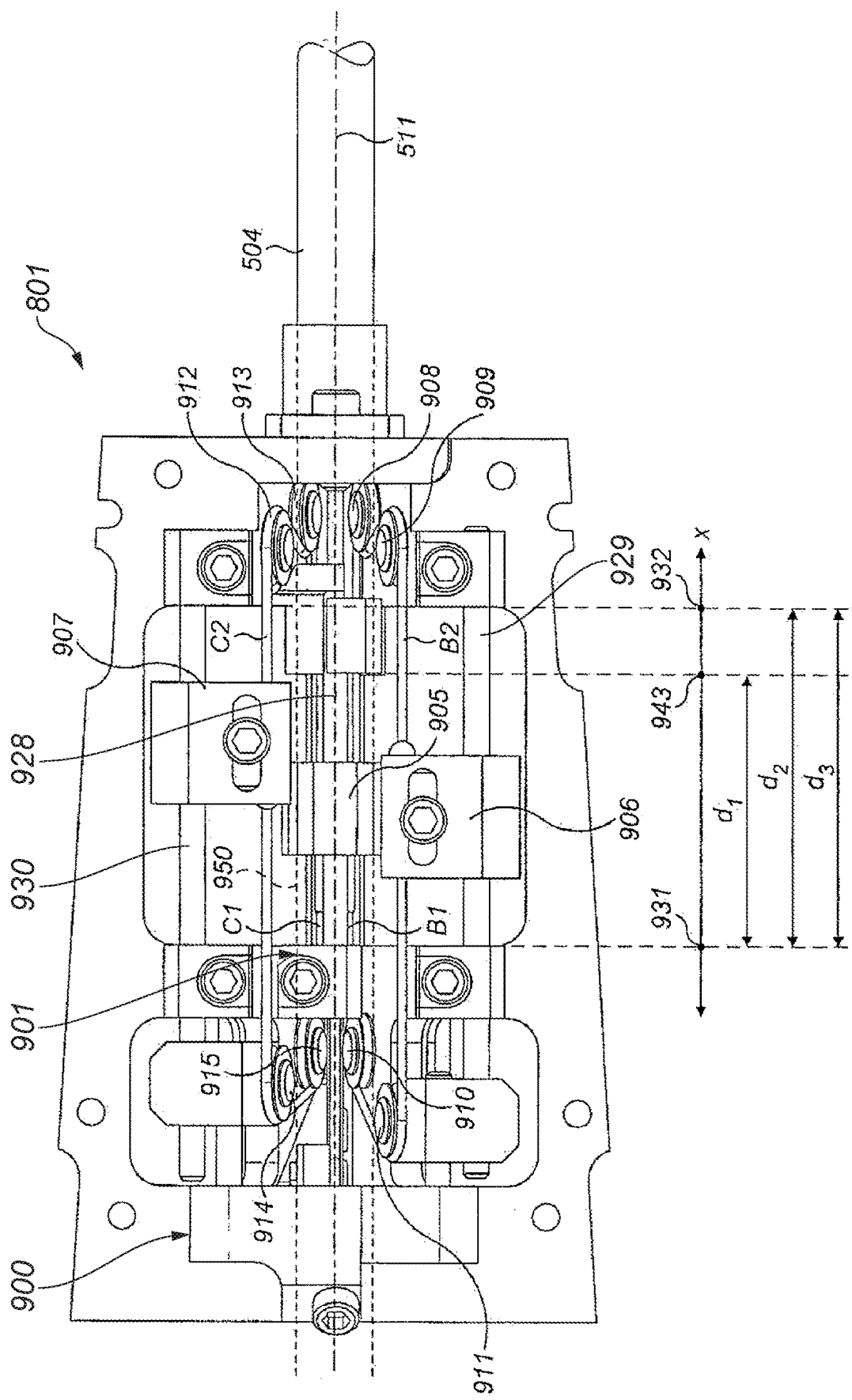
Figure 9C:
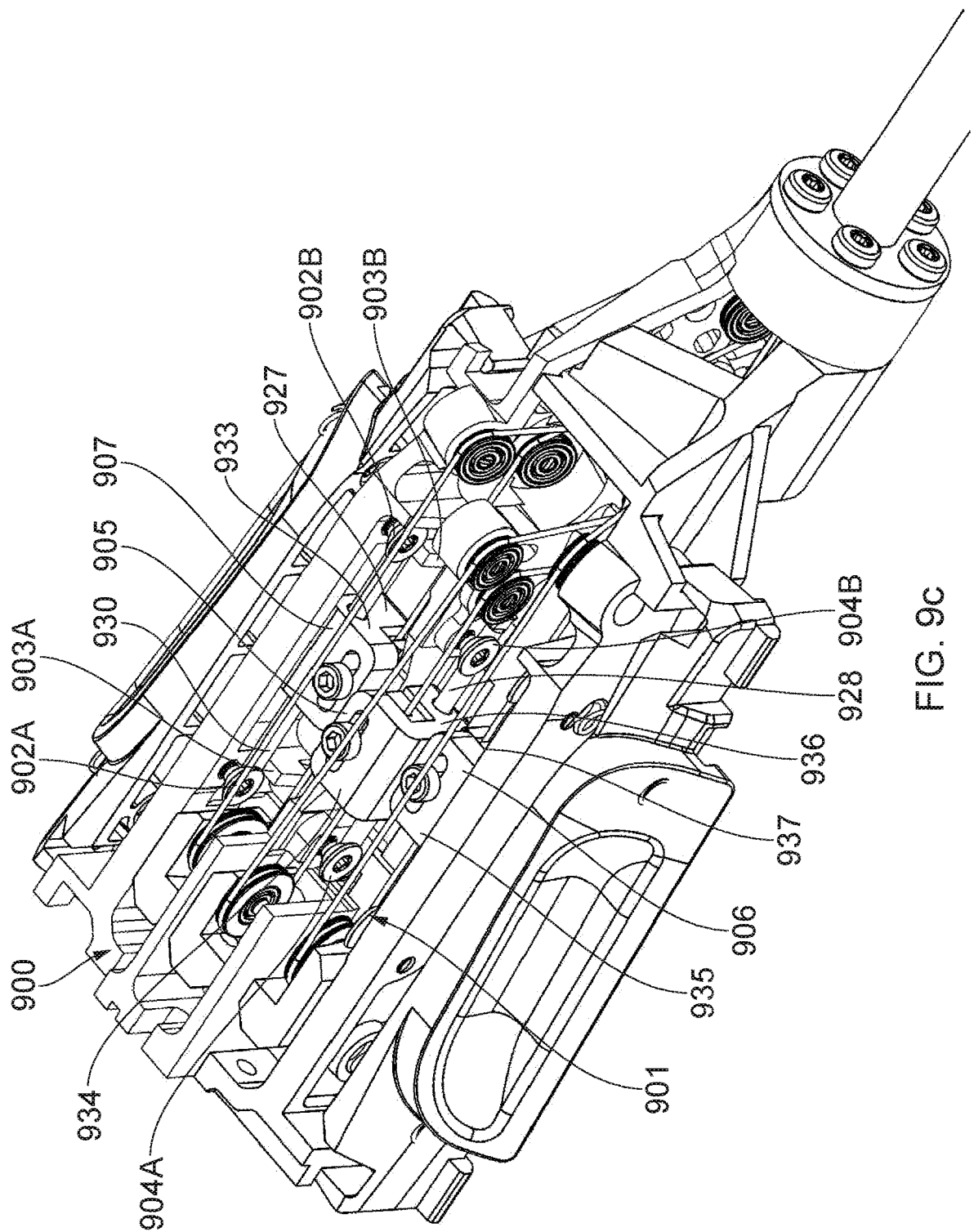

FIGS. 9a, 9b and 9c illustrate three more detailed views of the instrument interface 801.

The instrument interface 801 comprises a chassis 900 that supports a drive mechanism (denoted generally at 901) for driving the joints of the instrument articulation. The drive mechanism comprises an arrangement of drive elements and pulleys which transfer drive provided by the robotic arm to the joints, as will be described in more detail below.

As shown in FIGS. 9b and 9c, the instrument interface comprises three interface elements 905, 906 and 907. The instrument interface elements form part of the instrument interface drive mechanism. The first instrument interface element 905 engages the first pair of driving elements A1,A2. A second instrument interface element 906 engages the second pair of driving elements B1,B2. A third instrument interface element 907 engages the third pair of driving elements C1,C2. Each driving element is secured to its associated instrument interface element. In other words, each driving element is fast with its associated instrument interface element.

Thus, in the examples illustrated in FIGS. 9a, 9b and 9c, each pair of driving elements engages a single instrument interface element in the instrument interface 801. Each driving element engages an instrument interface element in the instrument interface. In other words, each driving element engages its own instrument interface element. A single instrument interface element drives a pair of driving elements. Each driving element is driven independently by a single instrument interface. In alternative arrangements, there may be a compound driving motion in which more than one instrument interface element drives a single driving element, a single instrument interface element drives more than one pair of driving elements, or a plurality of instrument interface elements collectively drive a plurality of driving elements.

The instrument interface elements 905, 906 and 907 are dispersed across the width of the instrument interface as shown in FIG. 9b. In the arrangement depicted in FIG. 9b, one instrument interface element 905 is within the internal portion 950 of the instrument interface. Specifically, the part of the instrument interface element 905 which engages the driving element is within the internal portion 950 of the instrument interface. The instrument interface element 905 as a whole may be substantially within the internal portion 950 of the instrument interface, as shown in FIG. 9b. The instrument interface element 905 as a whole may be wholly within the internal portion 950 of the instrument interface. The instrument interface element 905 is in this example aligned with the longitudinal axis 511 of the shaft 504. In an exemplary arrangement, only one instrument interface element is located within the internal portion of the instrument interface. The remainder of the instrument interface elements 906, 907 are within the external portion of the instrument interface. These other instrument interface elements 906, 907 are located on either side of the aligned instrument interface element 905. Specifically, the other instrument interface elements 906, 907 are located on either side of the aligned instrument interface element 905 in a direction perpendicular to the longitudinal axis of the shaft 511. The instrument interface elements 906 and 907 are not aligned with the longitudinal axis 511 of the shaft 504.

Instrument interface element 905 engages a first pair of driving elements A1, A2. As can be seen in FIG. 9a, between the proximal end of the shaft and the instrument interface element 905, the pair of driving elements A1, A2 lie wholly within the internal portion 950. Between the proximal end of the shaft and the instrument interface element 905, the pair of driving elements A1, A2 lie wholly parallel to the longitudinal axis of the shaft 511. In the arrangement shown, there are no intervening pulleys or other structures in the instrument interface around which the pair of driving elements A1, A2 is constrained to move between the proximal end of the shaft and the instrument interface element 1905. Only instrument interface element 905 engages its pair of driving elements A1, A2 in the internal portion 950 of the instrument interface in this arrangement.

Instrument interface element 906 engages a second pair of driving elements B1, B2. The instrument interface element 906 engages the second pair of driving elements B1, B2 in the external portion of the instrument interface.

Instrument interface element 907 engages a third pair of driving elements C1, C2. The instrument interface element 907 engages the third pair of driving elements C1, C2 in the external portion of the instrument interface.

A pulley arrangement is used to shift the driving elements over to engage with the instrument interface elements which are in the external portion. Each pair of driving elements engages a first pair of pulleys to shift it over from the proximal end of the shaft 504 to its respective instrument interface element, and a second pair of pulleys to shift it back from alignment with the instrument interface element to alignment with the shaft 504.

In the arrangement shown, the second pair of driving elements B1, B2 emerges from the proximal end of the shaft in a direction aligned with the shaft. The driving elements B1,B2 do not run exactly parallel to the longitudinal axis 511 of the shaft 504 as a result of the direction changes described with respect to FIG. 7. The second pair of driving elements B1, B2 is then constrained to move around pulley pair 908 and 909 to shift it from where it emerges from the shaft 504 to engagement with the second instrument interface element 906. The second pair of driving elements B1, B2 emerges from the pulley pair 908 and 909 in a direction parallel to and offset from the direction that the second pair of driving elements B1, B2 emerges from the proximal end of the shaft. The second pair of driving elements B1, B2 is constrained to move around pulley pair 910 and 911 to shift it from alignment with the second instrument interface element 906 to alignment with the shaft 504.

In the arrangement shown, the third pair of driving elements C1, C2 emerges from the proximal end of the shaft in a direction aligned with the shaft. The driving elements C1,C2 do not run exactly parallel to the longitudinal axis 511 of the shaft 504 as a result of the direction changes described with respect to FIG. 7. The third pair of driving elements C1,C2 is then constrained to move around pulley pair 912 and 913 to shift it from where it emerges from the shaft 504 to engagement with the third instrument interface element 907. The third pair of driving elements C1, C2 emerges from the pulley pair 912 and 913 in a direction parallel to and offset from the direction that the third pair of driving elements C1, C2 emerges from the proximal end of the shaft. The third pair of driving elements C1,C2 is constrained to move around pulley pair 914 and 915 to shift it from alignment with the third instrument interface element 907 to alignment with the shaft 504.

Thus, to summarise, in the arrangement shown in FIGS. 9a, 9b and 9c, pair of driving elements A1, A2 engage with the first instrument interface element 905. Pair of driving elements A1, A2 drive rotation of the articulation, and hence the end effector, about the first axis 510 (see FIG. 5a). The pair of driving elements B1, B2 engage with the second instrument interface 906. Driving elements B1,B2 drive rotation of the second joint 507. The pair of driving elements C1,C2 engage with the third instrument interface 907. Driving elements C1,C2 drive rotation of the third joint 513. Thus, each joint of the instrument articulation is driven by a respective pair of driving elements, and each pair of driving elements is in turn driven by a respective instrument interface element.

Each instrument interface element is displaceable within the instrument interface 801 to drive its respective pair of driving elements. Since each instrument interface element is secured to a corresponding pair of driving elements, a displacement of the instrument interface element is transferred to a displacement of the pair of driving elements. Each instrument interface element may be displaceable along the same line as the line of the pair of driving elements that it is secured to. Each instrument interface element engages with a corresponding drive assembly interface element of the robot arm. Thus, displacement of the instrument interface element is driven by the robot arm. In this way, the robot arm drives the pairs of driving elements (and hence the joints of the instrument articulation).

Each instrument interface element 905, 906 and 907 is linearly displaceable within the instrument interface 801. The interface elements may be displaceable along a displacement axis parallel to the longitudinal axis of the shaft 511. Each instrument interface element is mounted to a rail to support, or constrain, or guide, the motion of the interface element within the instrument interface. The rail may therefore be referred to as a guide bar. The rail/guide bar may be linear. As shown most clearly in FIGS. 9b and 9c, the first instrument interface element 905 is mounted to rail 928; the second instrument interface element 906 is mounted to rail 929; and the third instrument interface element 907 is mounted to rail 930. The interface elements are slideably mounted to the rails to permit relative linear motion between the rail and the interface elements. That is, each interface element 905, 906, 907 is slideable along its respective rail 928, 929, 930. The rails are fast with respect to the chassis 900, and thus the interface elements are slideable relative to the chassis.

Each instrument interface element can be displaced over a displacement range between a minimum displacement position and a maximum displacement position. For example, the minimum and maximum displacement positions may be determined by the ends of the rail along which the instrument interface element slides. The minimum and maximum displacement positions are labelled 931 and 932 on FIG. 9b for the second and third instrument interface elements 906 and 907. The minimum and maximum displacement positions are labelled 931 and 943 on FIG. 9b for the first instrument interface element 905. The first instrument interface element is linearly displaceable through a maximum distance $d_1$ minus the length of the first instrument interface element in the direction x. The second instrument interface element is linearly displaceable through a maximum distance $d_2$ minus the length of the second instrument interface element in the direction x. The third instrument interface element is linearly displaceable through a maximum distance $d_3$ minus the length of the third instrument interface element in the direction x. Here, $d_1 < d_2$ and $d_1 < d_3$, and $d_2 = d_3$.

In the example shown in FIG. 9, in the straight configuration of the instrument in which the end effector is aligned with the shaft, the first, second and third instrument interface elements 905, 906 and 907 are all located in the same plane perpendicular to the longitudinal axis of the shaft. Alternatively, in the straight configuration of the instrument, the first instrument interface element 905 may be centred in a different plane to the plane in which the second and third instrument interface elements 906, 907 are centred. This is because the midpoint of the travel of the first instrument interface element 905 over $d_1$ is offset from the midpoint of the travel of the second and third instrument interface elements 906, 907 over $d_2$, $d_3$.

Each instrument interface element comprises a body 933, 934, 935 and a lug 927, 936, 937. The body 933, 934, 935 is linearly displaceable between the minimum displacement position and the maximum displacement position of the instrument interface element. The pair of driving elements which engages the instrument interface element is secured to the lug of the instrument interface element. The lug is linearly displaceable within the body parallel to the direction along which the body is displaceable. The lug is linearly displaceable along the longitudinal direction x of the shaft parallel to the longitudinal axis 511 of the shaft.

The guide bars 928, 929 and 930 may be secured to the chassis 900. The guide bars may be secured to the chassis so that the motion of the instrument interface elements is tightly constrained during operation to remain linear and along the correct directional axis. This may reduce the risk of, for example, the driving elements slipping relative to the pulleys, and maintain the correction relationship between the displacement of the interface elements and rotation about a given joint.

The guide bars are secured to the chassis by securing elements. This can be seen most clearly in FIG. 9c for guide bars 930 and 928. Guide bar 930 is secured to the chassis by securing elements 902A and 902B, and guide bar 928 is secured to the chassis by securing elements 904A and 904B. Guide bar 929 is also secured to the chassis by a pair of securing elements (not shown in FIG. 9c). Thus, in the arrangement shown in FIG. 9, each guide bar is secured to the chassis by a pair of securing elements. The pair of securing elements for each guide bar may be located at opposing ends of the guide bar. The securing elements may be located at the terminal ends of the guide bar (i.e., a first securing element is located at a first terminal end of the guide bar, and a second securing element is located at a second terminal end of the guide bar). Securing the guide bar to the chassis with a pair of securing elements located at the terminal ends of the guide bar is convenient because it increases the useable length of the guide bar by not impeding the motion of the interface element along the guide bar.

To facilitate the securement of a guide bar to the chassis, the chassis may comprise a support element that interfaces with the guide bar along at least a portion of the length of the guide bar. The securing element and support element may then cooperate to secure the guide bar to the chassis. For example, the securing element may retain the guide bar against the support element to thereby secure the guide bar to the chassis. The chassis may comprise a plurality of support elements. Each securing element may retain a guide bar against a respective support element. Thus, the chassis may comprise a plurality of support elements for each guide bar.

In the example shown in FIG. 9c, the support elements are in the form of a corner feature. This can be seen most clearly for the guide bar 930, where the two corner features are denoted 903A and 903B. The guide bar is arranged so that the first corner feature 903A is located at a first terminal end of the guide bar 930, and the second corner feature is located at a second terminal end of the guide bar 930. Each corner feature defines a corner, and a securing element retains the guide bar in the corner to secure the guide bar to the chassis 900. Thus, securing element 902A retains the guide bar against the corner defined by corner feature 903A, and securing element 902B retains the guide bar against the corner defined by corner feature 903B. The corner features form part of the chassis 900. For example, the corner features may be integral with the remainder of the chassis body, or otherwise fixedly attached to the chassis body, The securing element 902A and corner feature 903A are shown in more detail in FIG. 10, which shows a cross-sectional view through the chassis 900. The remaining features of the instrument interface 801 (including securing element 902B and corner feature 903B) have been omitted from FIG. 10 for clarity.

The corner feature 903A comprises two surfaces 1001 and 1003 that define the corner. In this example, surfaces 1001 and 1003 are planar surfaces. The two surfaces 1001 and 1003 are shown here as being transverse to each other, however other angles between the two surfaces are possible. For example, the interior angle between the two surfaces (i.e. the angle defined by the surfaces against which the guide bar 930 is retained) may in general be less than 180 degrees. The angle between the two surfaces may be greater than or equal to 90 degrees, but less than 180 degrees. The angle between the two surfaces may be less than 90 degrees.

Conveniently, the two surfaces 1001 and 1003 meet to define a join 1005 that is parallel to the longitudinal axis of the shaft 511. In addition, the surface normal to both surface 1001 and 1003 may be transverse to the longitudinal axis of the shaft 511. Such an arrangement aligns the guide bar 930 within the instrument interface so that the longitudinal axis of the guide bar is parallel to the longitudinal axis of the shaft 511 when the guide bar is retained against the corner feature 903. Thus, the securing element 902A retains the guide bar in the corner defined by the corner feature 903A so that the join 1005 is parallel to the longitudinal axis of the guide bar 930, and the normal to surfaces 1001 and 1003 are transverse to the longitudinal axis of the guide bar 930.

In this example, the securing element 902A is a screw comprising a threaded shaft 1007 and a conical-shaped head 1009. The screw may be a countersunk screw, for example. The screw is screwed into the chassis (in particular, into the corner feature of the chassis) to secure the guide bar 930 to the chassis. The screw is screwed into the chassis parallel to the surface 1003. That is, the threaded shaft 1007 is parallel to the surface 1003 (i.e., the longitudinal axis of the threaded shaft is parallel to the surface 1003). Screwing the screw into the chassis parallel to the surface 1003 is advantageous because the conical-shaped head 1009 then secures the guide bar against the two surfaces 1001 and 1003 of the corner feature 903A (i.e. the securing element 902A pushes the guide rail 930 against both surfaces 1001 and 1003). This retains the guide bar 930 securely in the corner of the corner feature. More generally, the securing element 902A may comprise a shaft portion (which may be threaded or unthreaded), and a conical-shaped head. The shaft may be inserted into an insert, or bore, in one of the surfaces of the corner feature (e.g. in the example that the securing element is a bolt having a non-threaded shaft). Alternatively, the shaft may be screwed into the corner feature, e.g. in the example that the securing element is a screw having a threaded shaft.

It will be appreciated that the screw/bolt need not be inserted into the chassis parallel to the surface 1003, but could instead be inserted into the chassis parallel to the surface 1001. This would still enable the conical head 1009 to retain the guide bar 930 against both surfaces of the corner feature.

The corner feature may be made of a softer material than the securing element to enable the securing to be inserted into the corner feature. The corner feature may be made of the same material as the remainder of the chassis, or a different material.

The corner feature (and potentially the chassis) may for example be made of plastic, and the securing element may be made of metal.

Figure 10:
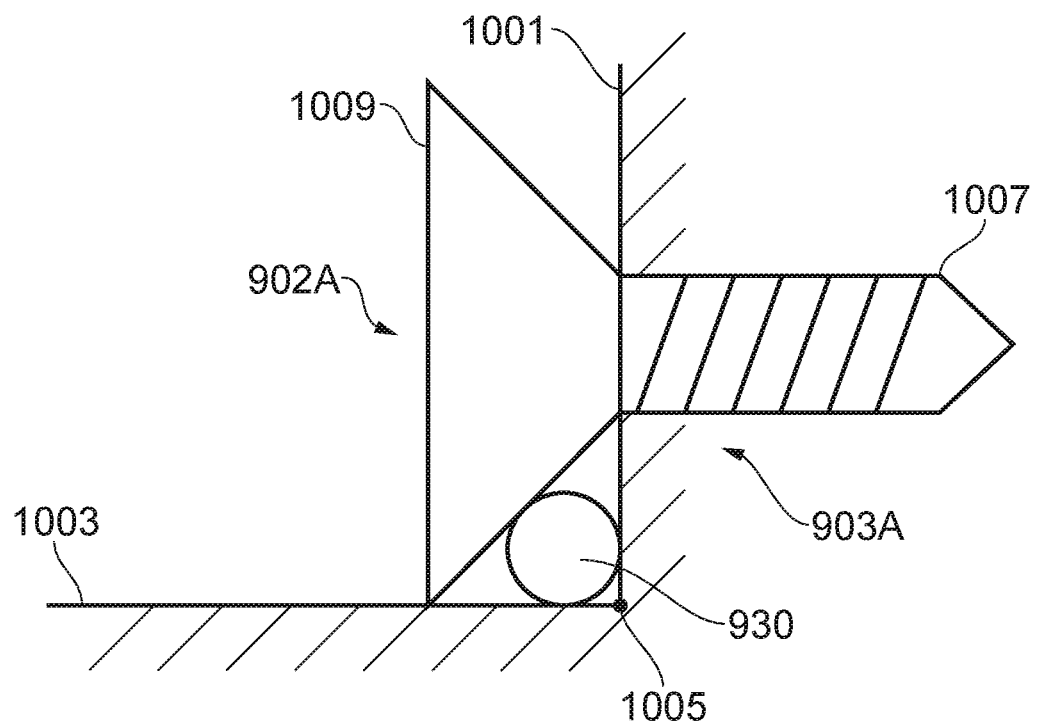
FIG. 10 illustrates a more detailed view of the supporting element and securing elements shown in FIG. 9.

Though only securing element 902A and corner feature 903A are shown in FIG. 10, it will be appreciated that the securing element 902B and corner feature 903B will take an analogous form. Furthermore, though the securing elements and support elements have been described in detail only for the guide bar 930, it will be appreciated that the securing elements and support elements for guide bars 928 and 929 may take an equivalent form.

The use of a corner feature and a securing element in the form of a screw or bolt having a conical-shaped head provides a low-cost yet effective approach to securing the guide rails to the chassis of the instrument interface. The conical-shaped head engages the guide rail to retain the guide rail against both surfaces of the corner feature. The use of two surfaces to retain the guide bar securely holds the guide bar in place, holding it in the desired orientation in which the longitudinal axis is parallel to the longitudinal axis of the shaft 511 to effect the transfer of linear drive through the instrument interface to the joints of the instrument.

In addition, tolerances in the location and/or orientation of the bore for the screw thread, and variations in the guide bar diameter can be accommodated by the securing element. For example, referring to FIG. 10, it can be appreciated that the shaft 1007 need not be inserted into the chassis exactly parallel to the surface 1003 for the conical head 1009 to retain the guide bar against both surfaces of the corner feature. So long as a normal to the conical surface of the head 1009 is non-transverse to the surface normals of both surfaces 1001 and 1003, the head 1009 can exert a retaining force on the guide bar against both surfaces 1001 and 1003. Tolerance in the location of the bore for receiving the shaft 1007 can also be accommodated. Though in the example shown in FIG. 10 the element 902A is inserted into the surface 1001 at a location such that the outer edge, or periphery, of the head 1009 abuts the other surface 1003, it will be appreciated that this is not necessary to secure the guide bar against the surfaces 1001 and 1003. The securing element 902A can still operate to retain the guide bar against the surfaces 1001 and 1003 if the screw is inserted into the surface so that there is clearance between the other surface 1003 and the outer edge of the head 1009. In other words, the design exemplified in FIG. 10 provides a certain degree of tolerance in the location and/or orientation of bore that receives the screw 1007. This may be useful for accommodating manufacturing errors.

Variations in the size of the guide bar diameter can also be accommodated, for example by varying the angle and/or location at which the element 902A is inserted into the surface 1001. Variations in guide bar diameter can also be accommodated by varying the amount by which the securing element 902A is inserted into the chassis. For example, if the screw shown in FIG. 10 was retracted from the position shown (so that only a portion of the shaft 1007 was inserted into the surface 1001), a guide rail with a larger diameter than that illustrated could be secured to the chassis. In other words, the design exemplified in FIG. 10 can accommodate variations in the diameter of the guide rail 930. This may be useful for providing a degree of flexibility in design and resilience to design changes, such as changing the diameter of the guide bar. Other forms of the support element and securing element for securing the guide bars to the chassis 900 are possible, examples of which will now be described.

Figure 11:
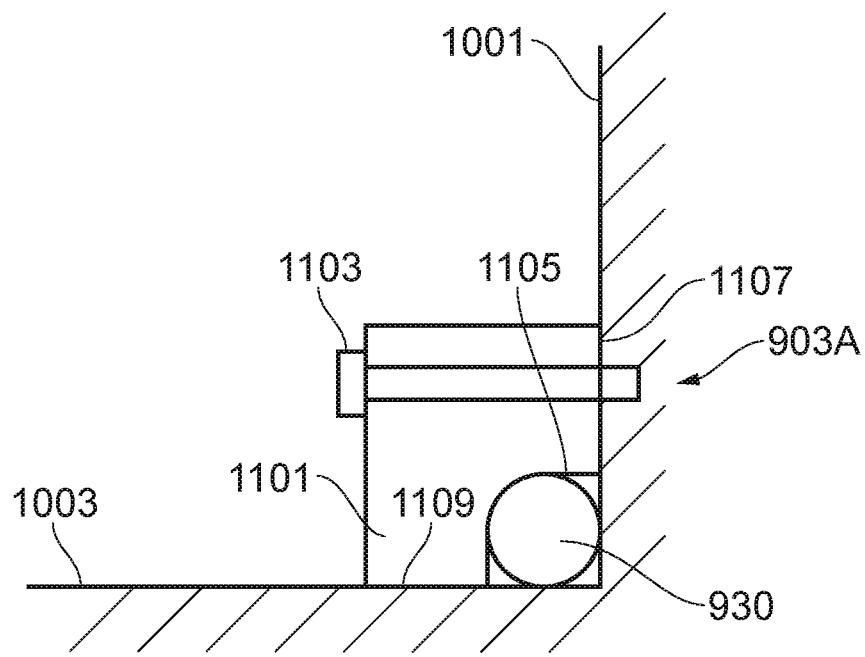
FIG. 11 illustrates an alternative example of the securing element.

FIG. 11 illustrates an example of an alternative form of securing element. FIG. 11 again shows a cross-section through the instrument interface in which a securing element, support element and guide rail are shown, but the remaining components of the instrument interface are omitted for clarity.

In this example, the support element is again in the form of a corner feature 903A comprising surfaces 1001 and 1003 defining a corner. However, in this example, the securing element comprises a retaining element 1101 and a clamping element 1103. The retaining element operates to retain the guide bar in the corner. The retaining element is secured to the chassis by the clamping element to thereby secure the guide bar to the chassis.

The retaining element 1101 is in the form of a block that comprises a first surface 1105 shaped to engage the guide bar 930. The first surface may complementary to the outer surface of the guide bar. The first surface could for example be a concave surface (e.g. if the guide bar is cylindrical). The first surface may be referred to as a guide bar surface (since this surfaces interfaces with the outer surface of the guide bar). The block 1101 further comprises second and third surfaces 1107, 1109 that engage a respective surface 1001, 1003 of the corner feature. The second and third surfaces may be angled so as to sit flush with the surfaces of the corner feature (i.e. both of the surfaces 1107, 1109 of the block 1101 sit flush with a respective surface 1001, 1003 of the corner feature). This form securing element is advantageous because the relatively large amounts of surface area contact with the corner feature and guide bar enable the guide bar to be securely held in place.

The clamping element 1103 fixes the retaining element 1101 to the corner feature. In this example, the clamping element is in the form of a bolt, or screw, that fixes the retaining element to a surface of the corner feature. In an alternative arrangement, the retaining element may be secured to the corner feature by a plurality of bolts or screws, for example by a first bolt/screw that fixes the retaining element 1101 to a first surface of the corner feature, and by a second bolt/screw that fixes the retaining element 1101 to a second surface of the corner feature.

In a variation of the arrangement shown in FIG. 11, the retaining element may take the form of block 1101, but rather than use a clamping element 1103, the block 1101 may be fixed to the corner feature by an adhesive, or be secured to the corner feature by some other means (e.g. by welding). Thus, in general, the securing element may comprise a retaining element that engages the outer surface of the guide bar and that is secured to the chassis 900 to thereby secure the guide bar to the chassis.

Figure 12:
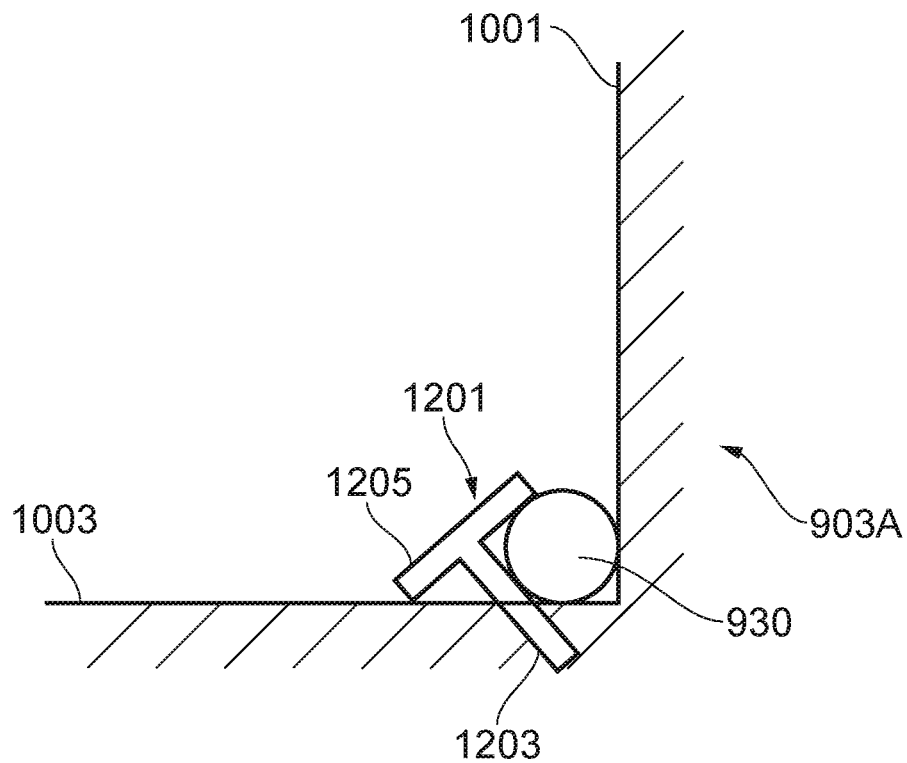
FIG. 12 illustrates another example of the securing element.

FIG. 12 illustrates a further example of an alternative form of securing element. FIG. 12 also shows a cross-section view through the instrument interface in which the remaining components of the instrument interface are omitted for clarity.

In this example, the support element again takes the form of a corner feature 903A comprising surfaces 1001 and 1003 defining a corner. The securing element in this example takes the form of a bolt 1201. The bolt comprises a shaft 1203 and a head 1205. Contrary to the example illustrated in FIG. 10, the bolt 1201 is inserted into the chassis non-parallel to both of the surfaces 1001 and 1003 of the corner feature. That is, the longitudinal axis of the shaft 1203 is non-parallel to both of the surfaces 1001 and 1003. The bolt may be inserted into the chassis diagonally to the surfaces 1001 and 1003 of the corner feature. That is, the longitudinal axis of the bolt shaft 1203 may be at an angle of 45 degrees to both surfaces 1001 and 1003. The bolt may be inserted into the chassis so that the shaft 1203 is flush with the outer surface of the guide rail 930. That is, the bolt does not pass through, i.e. is not inserted into, the guide rail. The shaft and the head cooperate to retain the guide bar 930 in the corner defined by the corner feature. The head 1205 may interface with the outer surface of the guide bar 930 to retain the guide bar in the corner. The bolt 1201 could be a pan head bolt. Alternatively, the securing element could be flat-headed screw.

The form of securing element exemplified in FIG. 12 may provide the same advantages of accommodating tolerances in the guide rail diameter and/or the position and location of the bore for receiving the shaft 1205 that were discussed above with respect to FIG. 10.

Figure 13:
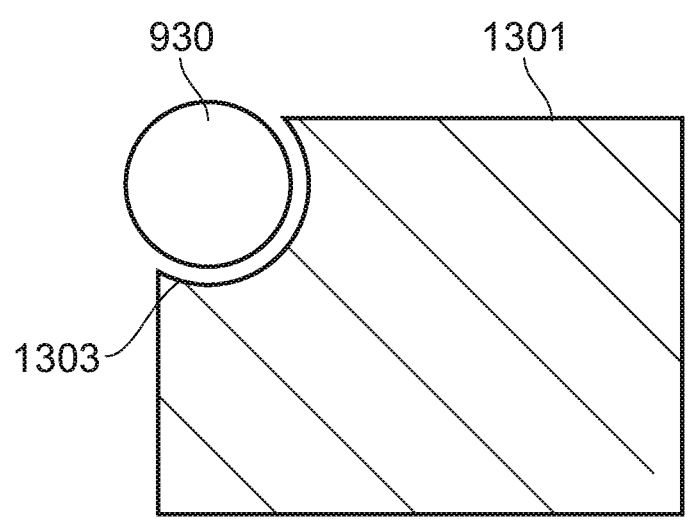
FIG. 13 illustrates an alternative example of the supporting element.

FIG. 13 illustrates an example of an alternative form of support element. FIG. 13 depicts a cross-sectional view through the instrument interface.

FIG. 13 shows a support element 130. The support element again forms part of the instrument interface chassis, but the remainder of the chassis has been omitted from the figure for the purposes of clarity. The support element 1301 comprises a curved surface 1303. The surface 1303 interfaces the guide bar 930 along at least a portion of the guide bar's length. The curved surface 1303 defines a channel in which the guide bar 930 sits. The curved surface therefore assists with retaining the guide bar against the chassis. The curved surface 1303 may be such that the normals to the surface are transverse to the longitudinal axis of the shaft 511. Thus, when the guide bar sits within the channel defined by the surface 1303, the surface normals to the channel are transverse to the longitudinal axis of the guide bar. The support element 1301 therefore operates to correctly orientate the guide bar within the instrument interface.

One or more securing elements (not shown in FIG. 13) may retain the guide bar 930 against the support element 1301 to thereby secure the guide bar to the chassis. The securing elements may take the form of one of the examples described above. The one or more securing elements could be countersunk screws, or flat-head screws or bolts inserted into the support element 1301, for example. There may be two securing elements inserted into the support element 1301 transversely to each other to secure the guide bar. Each securing element may comprise a shaft and a head (the longitudinal axes of the shaft being transverse to each other). Each head may engage the outer surface of the guide bar when the shafts are inserted into the support element 1301 to secure the guide bar against the support element.

Figure 14:
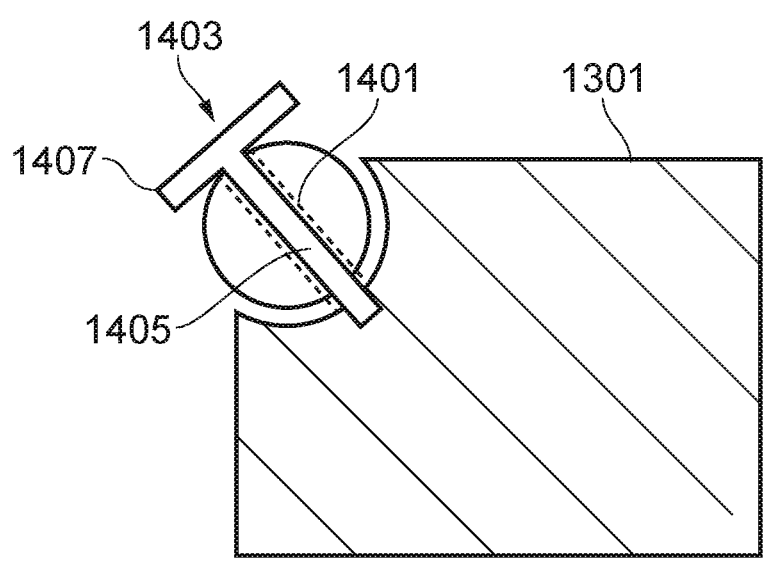
FIG. 14 illustrates an alternative example of the securement of a guide bar to the chassis of the instrument interface using a securing element.

In another example, shown in FIG. 14, a guide bar 930' comprises a bore 1401. The bore is located at a terminal end of guide bar. A securing element 1403 comprising a shaft 1405 and a head 1407 is inserted through the bore 1401 into the support element 1301 to secure the guide bar 930' to the support element. The bore 1401 may extend through the guide bar in a direction transverse to the longitudinal axis of the guide bar. The shaft 1405 may be threaded. In this case, the bore 1401 may also be threaded. When the securing element 1403 is inserted through the bore, the head 1407 engages the outer surface of the guide rail 930' to secure the guide rail to the support element. The securing element could be a bolt, or screw. This arrangement may have the advantage of increasing the strength at which the guide bar is secured to the chassis.

It will be appreciated that the guide bar 930' (comprising bore 1401) and securing element 1403 may also be used with a support element in the form of a corner feature, such as corner feature 903A shown in FIG. 10. In this case, the bore 1401 could be parallel to one of the surfaces 1001 and 1003 of the corner feature. Alternatively, the bore 1401 could be angled relative to both surfaces 1001 and 1003 (i.e. non-parallel to both surfaces) so that the securing element 1403 retains the guide bar against both surfaces of the corner feature, rather than just a single surface. The head 1407 of the securing element may be sized so that, when the securing element is inserted through the bore into the corner feature, the head engages both surfaces 1001 and 1003 of the corner feature.

If the guide bar comprises a bore, then the chassis 900 may not include support elements. Instead, the guide bars may be secured to the chassis directly by virtue of a securing element that is inserted through the bore into the chassis.

Figure 15:
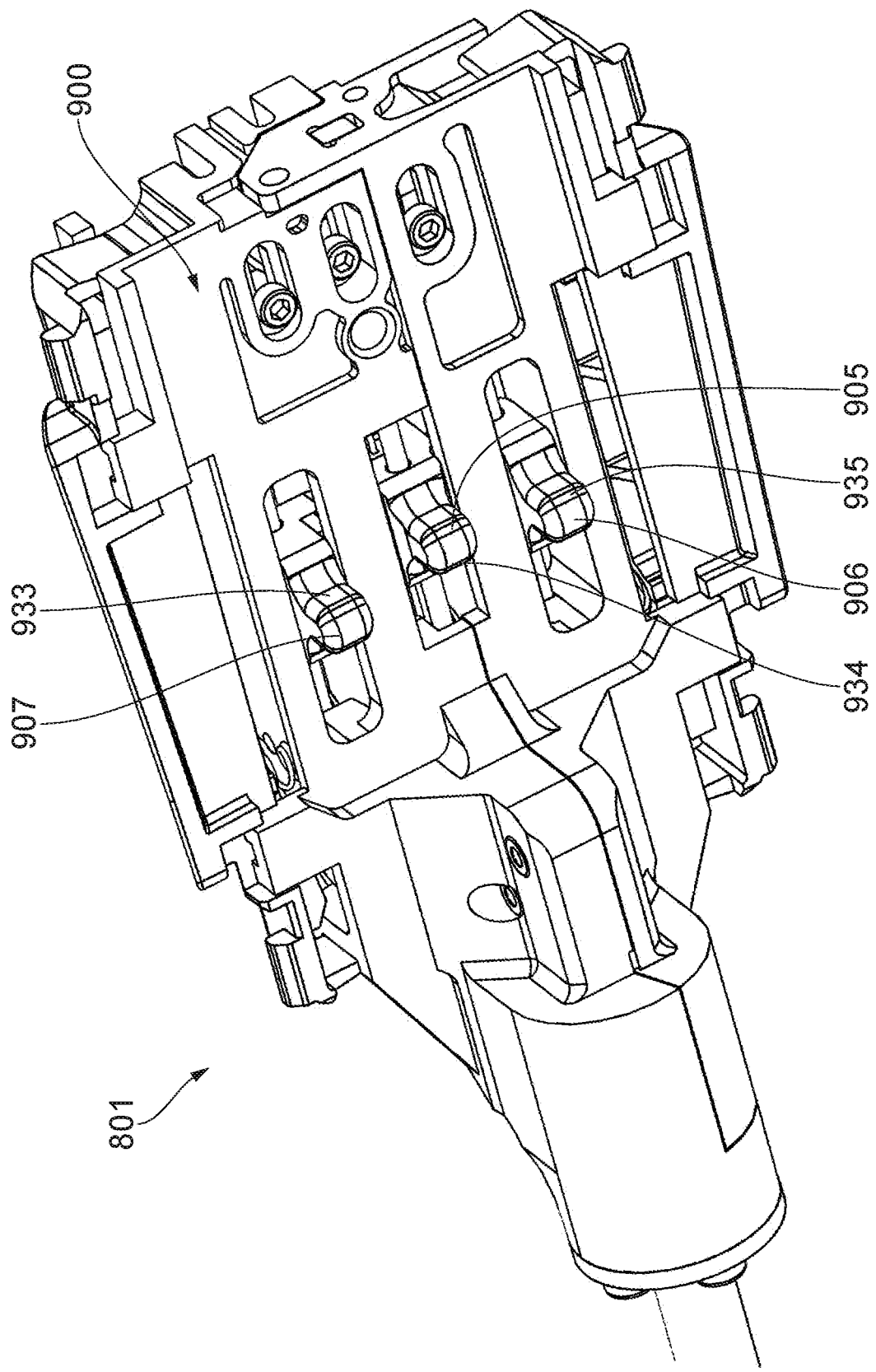
FIG. 15 is a view of the underside of the instrument interface.

FIG. 15 shows an underside view of the instrument interface 801. It can be seen that the underside of the instrument interface bodies 933, 934 and 935 of interface elements 905, 906, 907 are in the form of projections. The bodies may project below the plane defined by the underside of the chassis 900. Each instrument interface body 933, 934, 935 is receivable in a corresponding socket of a drive assembly interface element. The shapes of the body and socket correspond such that when the drive assembly interface element is displaced, this displacement is transferred to the instrument interface element without any slippage. Thus, the body fits snugly into the socket along at least one line in the displacement direction. The instrument interface element may be displaceable over the same displacement range as its corresponding drive assembly interface element.

Figure 16A:
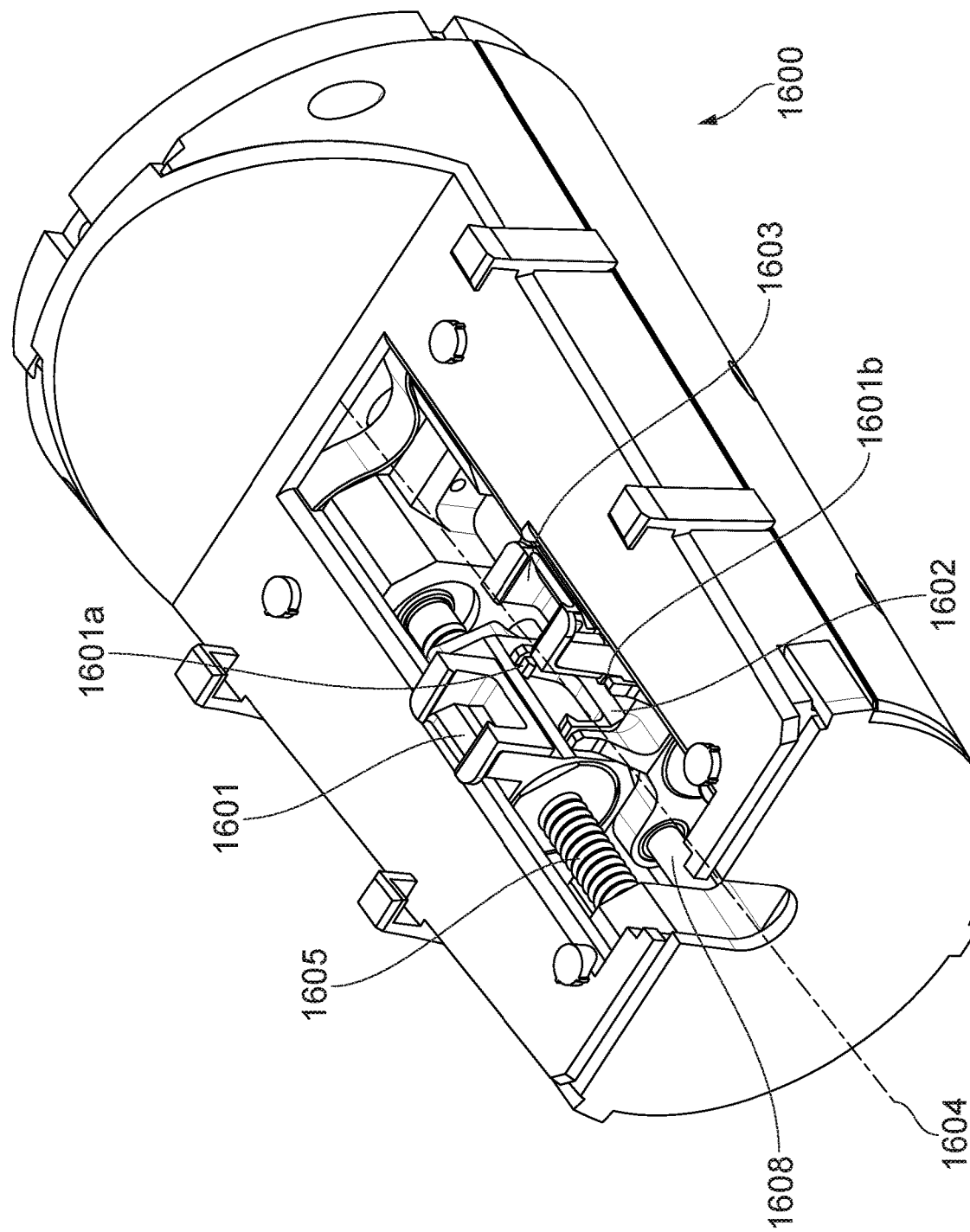
FIGS. 16a, 16b and 16c illustrate three views of a drive assembly interface of a robot arm.
Figure 16B:
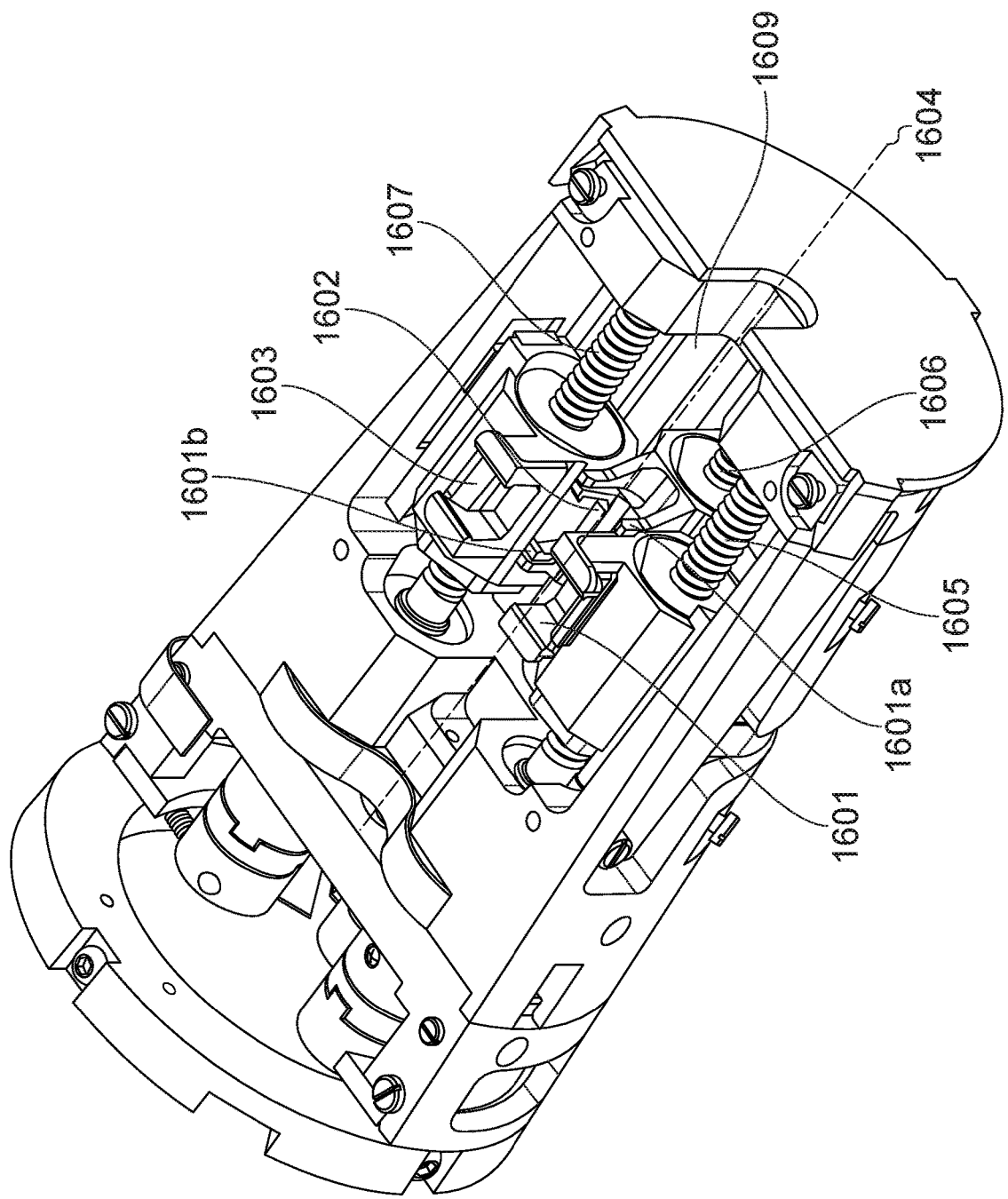
Figure 16C:
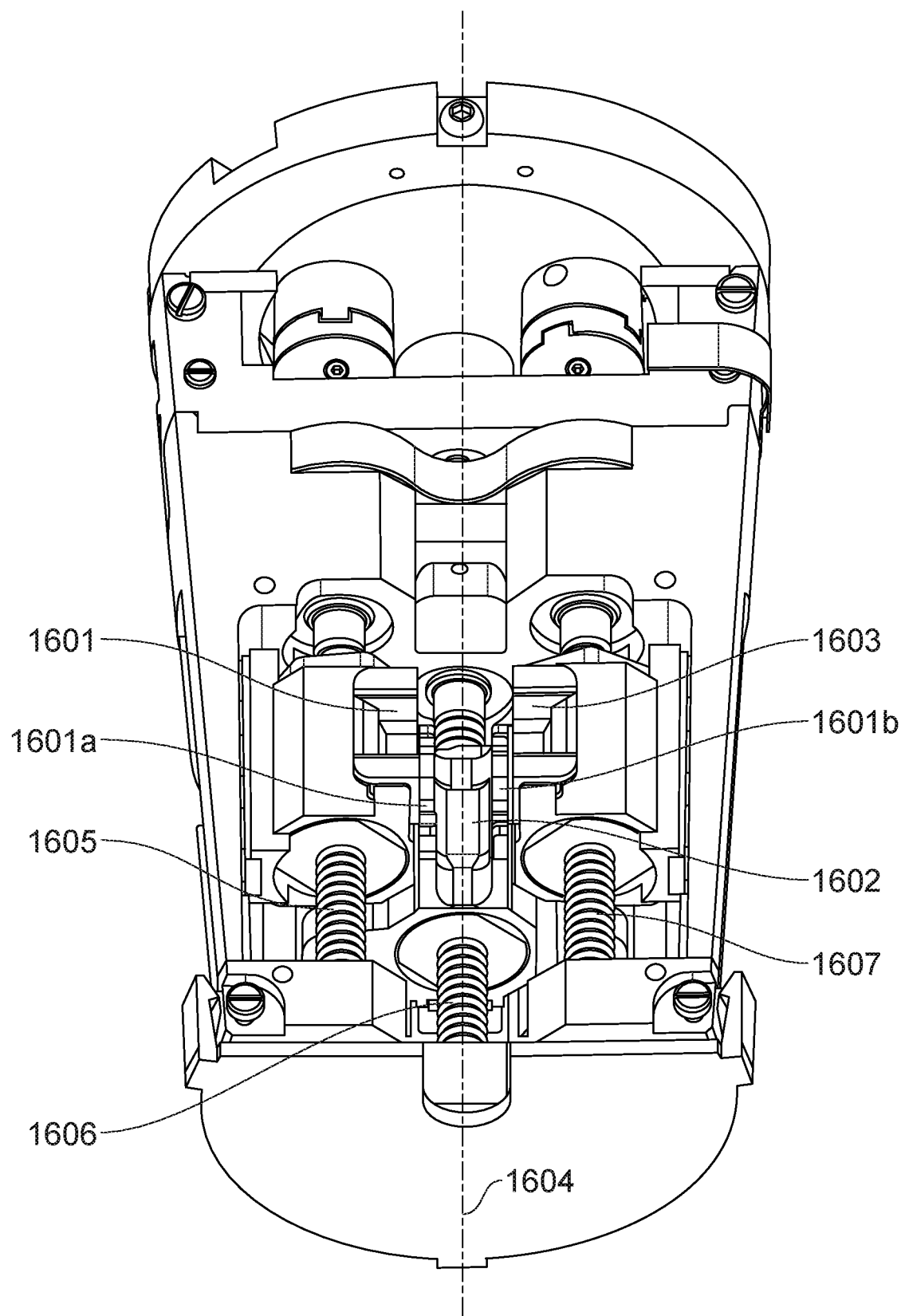

FIGS. 16*a*, 16*b* and 16*c* illustrates a drive assembly interface 1600. The drive assembly interface is at the terminal end of the terminal link of the robot arm. That terminal link is connected to the link next to it by a roll joint. The roll joint permits the terminal link to rotate about a longitudinal axis 1604 of the terminal link. Drive assembly interface 1600 comprises drive assembly interface elements 1601, 1602 and 1603. The drive assembly interface elements are configured to receive instrument interface elements 905, 906 and 907. First drive assembly interface element 1602 is configured to receive first instrument interface element 905. Second drive assembly interface element 1601 is configured to receive second instrument interface element 906. Third drive assembly interface element 1602 is configured to receive third instrument interface element 907.

Figure 17:
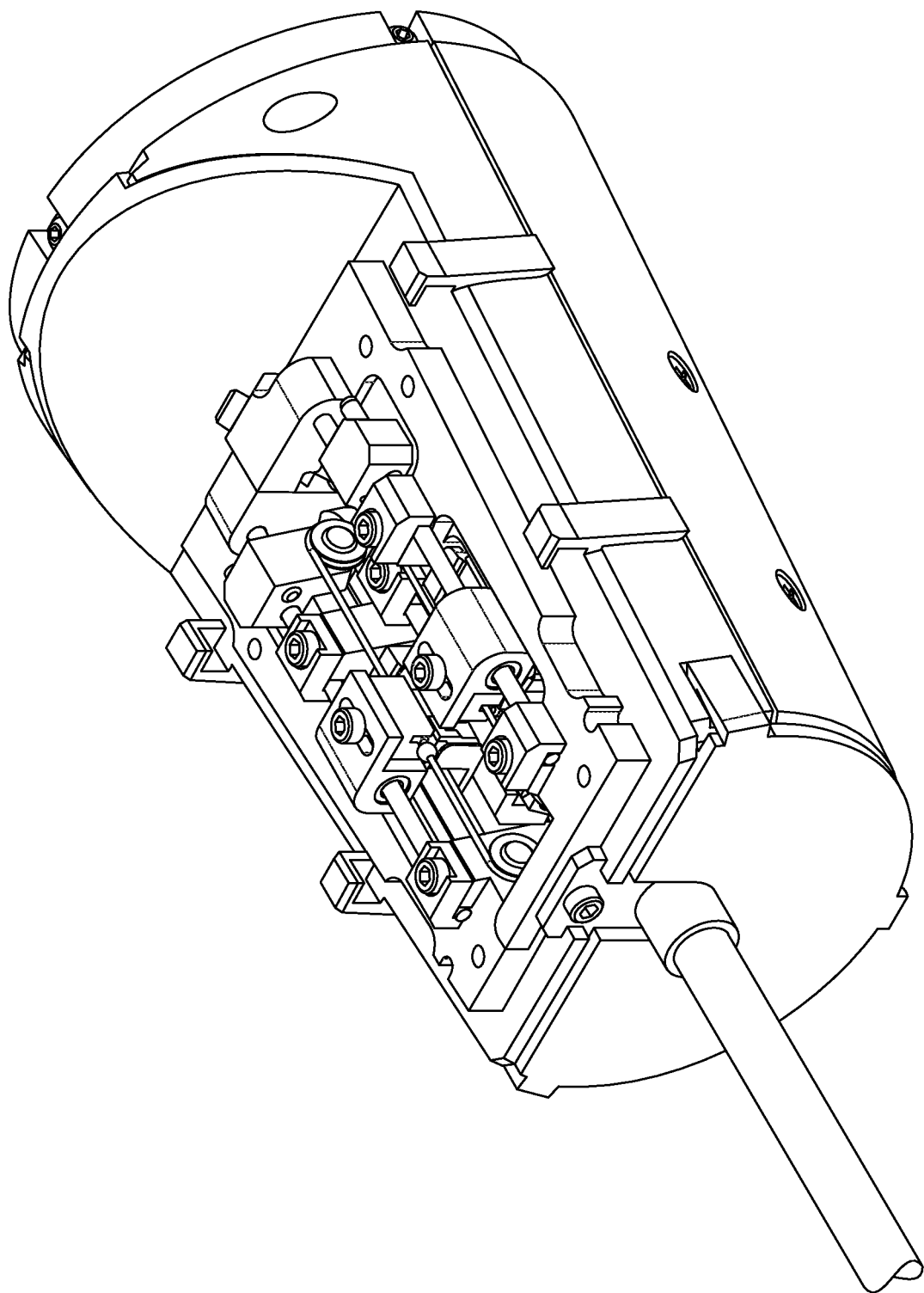
FIG. 17 illustrates an instrument interface engaged in a drive assembly interface.

Each drive assembly interface element is displaceable along a direction parallel to the longitudinal axis 1604 of the drive assembly. Each drive assembly interface element is displaceable over a displacement range. When the instrument interface is seated in the drive assembly, as shown in FIG. 17, each drive assembly interface element is displaceable in the same direction as the direction in which the instrument interface element that it engages with is displaceable in.

The first drive assembly interface element 1602 engages the first instrument interface element 905 on the longitudinal axis 1604 of the drive assembly. Thus, the first drive assembly interface element 905 drives the first instrument interface element 905 along the longitudinal axis of the drive assembly, and hence along the longitudinal axis of the terminal link of the robot arm. Suitably, of all the drive assembly interface elements in the drive assembly, only the first drive assembly interface element 1602 is displaceable along the longitudinal axis 1604 of the terminal link. The first instrument interface element 905 drives the first pair of driving elements A1, A2 to drive rotation of the distal end of the instrument about the first axis 510 which is perpendicular to the instrument shaft axis 511. When the instrument interface 801 is seated in the drive assembly 1600, the longitudinal axis 511 of the instrument shaft is parallel to the longitudinal axis 1604 of the terminal link. Suitably, the longitudinal axis 511 of the instrument shaft is coincident with the longitudinal axis 1604 of the terminal link.

The second drive assembly interface element 1601 engages the second instrument interface element 906 on an axis parallel to but offset from the longitudinal axis 1604 of the drive assembly. The second drive assembly interface element 1601 is displaceable along this axis so as to drive the second instrument interface element 906 along this axis. The second instrument interface element 906 drives the second pair of driving elements B1, B2 to drive rotation of an end effector element 502 about the second joint 507.

The third drive assembly interface element 1603 engages the third instrument interface element 907 on an axis parallel to but offset from the longitudinal axis 1604 of the drive assembly. The third drive assembly interface element 1603 is displaceable along this axis so as to drive the third instrument interface element 907 along this axis.

The third instrument interface element 907 drives the third pair of driving elements C1, C2 to drive rotation of the end effector element 503 about the third joint 513.

The drive assembly interface elements may releasably engage the corresponding instrument interface elements.

The drive assembly depicted in FIGS. 16a, 16b and 16c may drive the instrument interface depicted in FIGS. 9a, 9b and 9c which in turn drives the first, second and third joints depicted in FIGS. 5a and 5b, such that the first drive assembly interface element 1602 drives the first joint 506, the second drive assembly interface element 1601 drives the second joint 507, and the third drive assembly interface element 1603 drives the third joint 513. In an alternative arrangement, the drive assembly interface elements may drive different joints. For example, if the first pair of driving elements A1, A2 are connected to the second instrument interface element 906, then the second drive assembly interface element 1601 drives the first joint 506. If the second pair of driving elements B1, B2 are connected to the first instrument interface element 905, then the first drive assembly interface element 1602 drives the second joint 507. In this example, the third pair of driving elements C1, C2 are connected to the third instrument interface element 907, so that the third drive assembly interface element 1603 drives the third joint 513. In this example, the first drive assembly interface element 1602 is linearly displaceable through a maximum distance $s_1$. The second drive assembly interface element 1601 is linearly displaceable through a maximum distance $s_2$. The third drive assembly interface element 2103 is linearly displaceable through a maximum distance 53. Suitably $s_2 < s_1$ and $s_2 < s_3$. Suitably, $s_1 = s_3$.

In the examples described herein the drive assembly interface included three drive assembly interface elements that transferred drive to three instrument interface elements that transferred drive to three joints of the articulation at the distal end of the instrument shaft. It will be appreciated that the drive assembly interfaces described herein could be modified to include further or fewer drive assembly interface elements to transfer drive to further or fewer instrument interface elements. The instrument interfaces described herein could be modified to include further or fewer instrument interface elements to transfer drive to further or fewer joints of the articulation at the distal end of the instrument shaft. The articulation itself could also be modified to include further or fewer joints. Thus, the instrument interface may include a greater or fewer number of guide bars than in the examples described herein. The instrument interface may for example include a single guide bar (having mounted thereon a single instrument interface element).

It will also be appreciated that the end effector may only have one end effector element. In this case, the articulation does not include the third joint 513, the instrument interface does not include an instrument interface element for driving the third joint, and the drive assembly does not include a drive assembly interface element for driving that instrument interface element.

The instrument could be used for non-surgical purposes. For example, it could be used in a cosmetic procedure.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. A robotic surgical instrument, comprising:
a shaft;
an articulation at a distal end of the shaft configured to articulate an end effector, the articulation comprising a joint being driveable by a pair of driving elements; and
an instrument interface at a proximal end of the shaft, the instrument interface comprising:
a chassis;
an instrument interface element slideable along a guide bar to drive the pair of driving elements to thereby drive the joint of the articulation to articulate, wherein the pair of driving elements are fast with respect to the interface element so that a displacement of the instrument interface element with respect to the guide bar is transferred to the pair of driving elements;
the chassis comprising a support element configured to interface the guide bar along at least a portion of its length; and
a securing element configured to retain the guide bar against the support element to thereby secure the guide bar to the chassis.

2. A robotic surgical instrument as claimed in claim 1, wherein the support element comprises a curved surface that interfaces the guide bar along at least a portion of its length, wherein the support element is arranged so that each surface normal to the curved surface is transverse to a longitudinal axis of the guide bar.

3. A robotic surgical instrument as claimed in claim 1, wherein the support element is a corner feature defining a corner, and the securing element retains the guide bar in the corner to secure the guide bar to the chassis, wherein the corner feature comprises two surfaces that define the corner.

4. A robotic surgical instrument as claimed in claim 3, wherein the two surfaces are planar.

5. A robotic surgical instrument as claimed in claim 3, wherein the two surfaces are transverse to each other.

6. A robotic surgical instrument as claimed in claim 3, wherein the angle between the two surfaces is less than 180 degrees.

7. A robotic surgical instrument as claimed in claim 3, wherein the angle between the two surfaces is greater than or equal to 90 degrees and less than 180 degrees.

8. A robotic surgical instrument as claimed in claim 3, wherein the angle between the two surfaces is less than or equal to 90 degrees.

9. A robotic surgical instrument as claimed in claim 3, wherein the two surfaces meet to define a join that is parallel to a longitudinal axis of the instrument shaft.

10. A robotic surgical instrument as claimed in claim 3, wherein the securing element comprises a shaft and a head, the shaft being inserted into the corner feature at an angle to both surfaces of the corner feature so that a longitudinal axis of the shaft is non-parallel to both surfaces, wherein the shaft is inserted into the corner feature diagonally to the surfaces of the corner feature.

11. A robotic surgical instrument as claimed in claim 1, wherein the securing element comprises a shaft portion and a conical-shaped head, the shaft portion being inserted into the chassis to secure the guide bar to the chassis.

12. A robotic surgical instrument as claimed in claim 11, wherein the support element is a corner feature defining a corner, and the securing element retains the guide bar in the corner to secure the guide bar to the chassis, wherein the corner feature comprises two surfaces that define the corner, and the shaft portion is inserted into the chassis parallel to one of the surfaces of the corner feature wherein the shaft portion is inserted into the chassis so that the conical-shaped head secures the guide bar against the two surfaces of the corner feature.

13. A robotic surgical instrument as claimed in claim 11, wherein the shaft portion is a threaded shaft portion.

14. A robotic surgical instrument as claimed in claim 11, wherein the securing element is a countersunk screw or bolt.

15. A robotic surgical instrument as claimed in any of claim 1, wherein the securing element comprises a retaining element having a first surface shaped to engage the guide bar and being secured to the chassis to thereby secure the guide bar to the chassis.

16. A robotic surgical instrument as claimed in claim 15, wherein the support element is a corner feature defining a corner, and the securing element retains the guide bar in the corner to secure the guide bar to the chassis, wherein the corner feature comprises two surfaces that define the corner, and the retaining element is a block comprising second and third surfaces angled to interface the surfaces of the corner feature.

17. A robotic surgical instrument as claimed in claim 1, wherein the guide bar comprises a bore, and the securing element is a screw or bolt inserted into the support element through the bore to secure the guide bar to the chassis.

18. A robotic surgical instrument as claimed in claim 1, wherein the instrument interface element is linearly slideable along the guide bar, and wherein the instrument interface element is linearly slideable along a longitudinal axis of the guide bar parallel to a longitudinal axis of the shaft.

19. A robotic surgical instrument as claimed in claim 1, wherein the instrument interface further comprises a second securing element to secure the guide bar to the chassis, wherein the two securing elements are located at opposing ends of the guide bar.

20. A robotic surgical instrument as claimed in claim 19, wherein the chassis comprises a second support element, and the second securing element retains the guide bar against the second support element to secure the guide bar to the chassis.

* * * * *